(12) United States Patent
Dale et al.

(10) Patent No.: US 8,778,697 B2
(45) Date of Patent: Jul. 15, 2014

(54) METHOD OF MEASURING THE AFFINITY OF BIOMOLECULES

(75) Inventors: Trevor Clive Dale, Cardiff (GB); Adrian John Harwood, Cardiff (GB); Paola Borri, Cardiff (GB)

(73) Assignee: Nanotether Discovery Science Limited, Cardiff (GB)

( * ) Notice: Subject to any disclaimer, the term of this patent is extended or adjusted under 35 U.S.C. 154(b) by 911 days.

(21) Appl. No.: 12/094,073

(22) PCT Filed: Nov. 10, 2006

(86) PCT No.: PCT/GB2006/004208
§ 371 (c)(1),
(2), (4) Date: Sep. 9, 2008

(87) PCT Pub. No.: WO2007/057644
PCT Pub. Date: May 24, 2007

(65) Prior Publication Data
US 2009/0023227 A1 Jan. 22, 2009

(30) Foreign Application Priority Data
Nov. 16, 2005 (GB) .................................. 0523366.3

(51) Int. Cl.
*G01N 33/53* (2006.01)
(52) U.S. Cl.
USPC .................................. 436/501; 435/4; 435/7.1
(58) Field of Classification Search
None
See application file for complete search history.

(56) References Cited

U.S. PATENT DOCUMENTS

2002/0150947 A1  10/2002  Erlanson et al.
2004/0171069 A1 *  9/2004  Cook et al. ..................... 435/7.1

FOREIGN PATENT DOCUMENTS

WO        2004/038415        5/2004

OTHER PUBLICATIONS

Axelrod, D., "Surface fluorescence microscopy with evanescent illumination," Light Microscopy in Biology, Lacey, A. (ed), Oxford University Press, New York, pp. 399-423 (1999).
Bustamante, C., "Entropic Elasticity of λ-Phage DNA," Science, vol. 265, pp. 1599-1600 (1994).
Chrisey, L.A. et al., "Covalent attachment of synthetic DNA to self—assembled monolayer films," Nucleic Acids Research, vol. 24, pp. 3031-3039 (1996).
Goldstien, B. et al., "The influence of transport on the risk kinetics of binding to surface receptors: application to cells and BIAcore," Journal of Molecular Recognition, Heyden & Son, Ltd., London, GB, vol. 12, No. 5, Sep. 1999, pp. 293-299 XP002252376.
Hodneland et al., "Selective immobilization of proteins to self-assembled monolayers presenting active site-directed capture ligands," Proceedings of the National Academy of Science, vol. 99, pp. 5048-5052 (2002).
Jian et al., "A combined wormlike-chain and bead model for dynamic simulations of long linear DNA," Journal of Computational Physics, vol. 136, pp. 168-179 (1997).
Jung et al., "Covalent attachment and hybridization of DNA oligonucleotides on patterned single-walled carbon nanotube films," Langmuir, vol. 20, No. 20, pp. 8886-8891 (2004).
Jung, G. et al., "A functional protein chip for pathway optimization and in vitro metabolic engineering," Science, pp. 428-431 (2004).
Keppler et al., "Labeling of fusion proteins of 06-alkylguanine-DNA alkyltransferase with small molecules in vivo and in vitro," Methods, vol. 32, pp. 437-444 (2004).
Keppler et al., "Labeling of fusion proteins with synthetic fluorophores in live cells," Proceedings of the National Academy of Science, vol. 101, pp. 9955-9959; (2004) .
Labean et al., "Construction, Analysis, Ligation, and Self-Assembly of DNA Triple Crossover Complexes," Journal of American Chemical Society, vol. 122, pp. 1848-1860, (2000).
Marko, J. F., and Sigga, E. D., Stretching DNA. Macromolecules, vol. 28, pp. 8759-8770 (1995).
Morgan et al., "Fluorescence Lifetime Imaging: An emerging technique in fluorescence Microscopy", Chromosome Research, vol. 4, No. 4, pp. 261-263 (1996).
Roberts, R. W. et al., "RNA-peptide fusions for the in vitro selection of peptides and proteins," Proceedings of the National Academy of Science, vol. 94, pp. 12297-12302 (1997).
Santalucia, Jr et al, The Annual Review of Biophysics and Biomolecular Structure, vol. 33, pp. 415-440 (2004).
Temple et al., "From genome to proteome: developing expression clone resources for the human genome," Human Molecular Genetics, vol. 15, Review Issue No. 1, pp. R31-R43 (2006).
Walter, Nils G. et al., "In the fluorescent spotlight: global and local conformational changes of small catalytic RNAs," Biopolymers (Nucleic Acid Sciences), vol. 61, No. 3 (2001) pp. 224-242 XP009084951.
International Search Report for International Patent Application PCT/GB2006/004208 mailed Jun. 21, 2007.
Perrins, R.D. et al., "Doing More with less: A Method for Low Total Mass, Affinity Measurement Using Variable-Length Nanotethers," Anal. Chem., vol. 83, pp. 8900-8905 (2011).

\* cited by examiner

*Primary Examiner* — Galina Yakovleva
(74) *Attorney, Agent, or Firm* — Hunton & Williams LLP

(57) ABSTRACT

The invention provides a method of measuring the affinity of first and second biomolecules in which a first biomolecule is tethered by a first tether portion having a first tether portion length and a second biomolecule is tethered by a second tether portion having a second tether portion length, the method comprising determining binding of adjacent first and second biomolecules to each other, varying at least one of the first and second tether lengths and determining binding of the first and second biomolecules. The invention also provides apparatus suitable for use in the method of the invention.

25 Claims, 22 Drawing Sheets

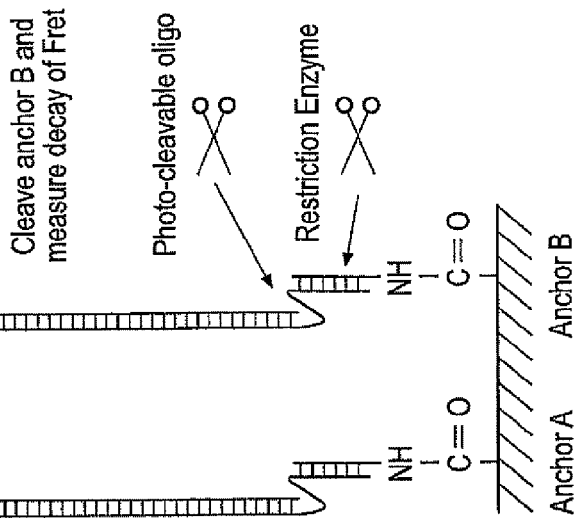
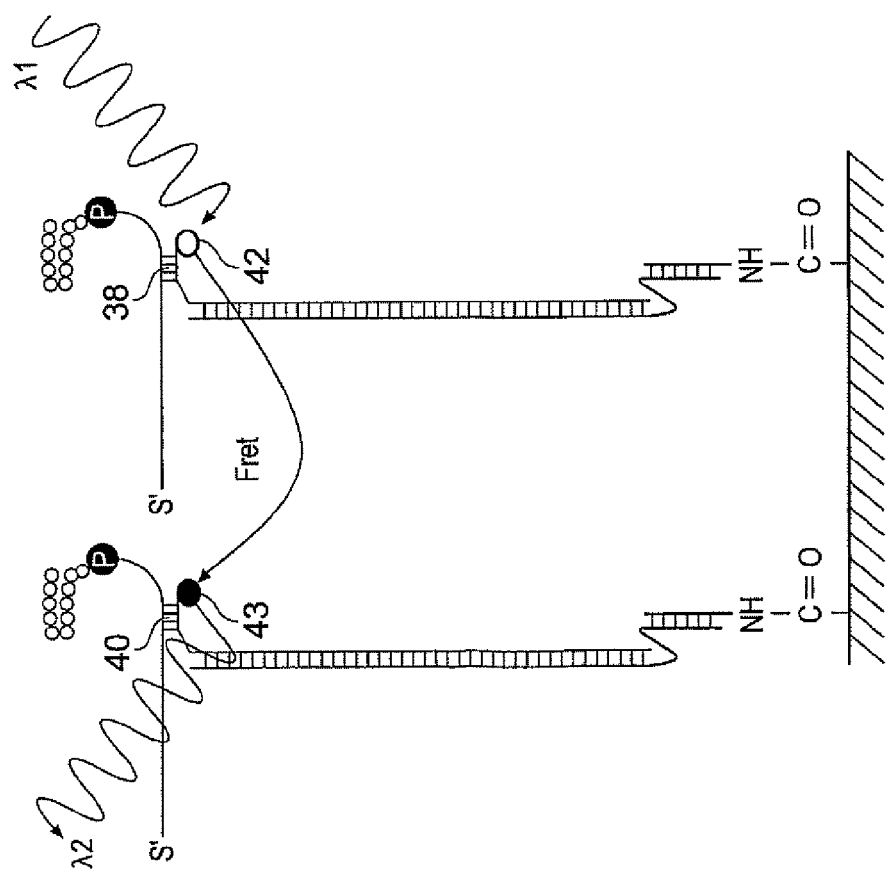
Fig. 11
Fig. 10

A  Varying concentrations of A and B by altering tether length

B  Bound and Free tethered pairs

C  Bound and Free inter-molecular interactions

| Length p [bp] | f=[AD]/ D | U | R | τ [ns] | [A]$_{TOT}$ [nM] | [D]$_{TOT}$ [nM] | [A] [nM] |
|---|---|---|---|---|---|---|---|
| 710 | 0.1181 | 0.8905 | 0.134 | 0.5569 | 778.15 | 778.15 | 686.25 |
| 515 | 0.2922 | 0.7299 | 0.413 | 0.6724 | 2039.0 | 2039.0 | 1443.2 |

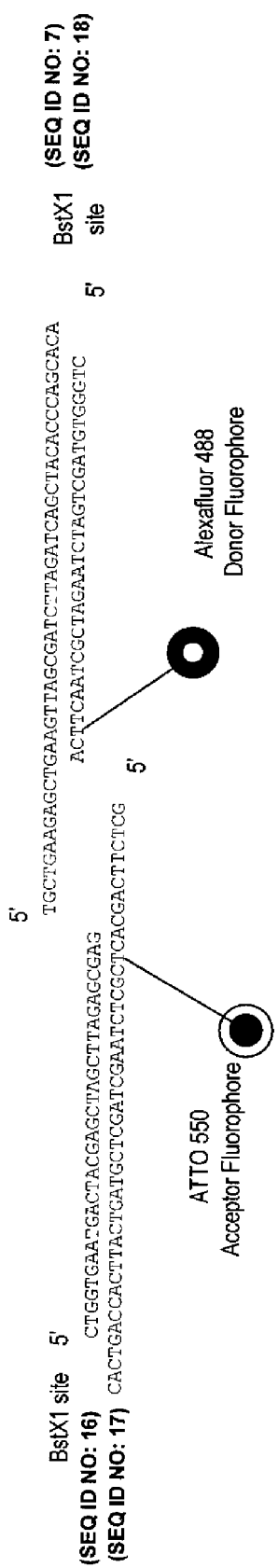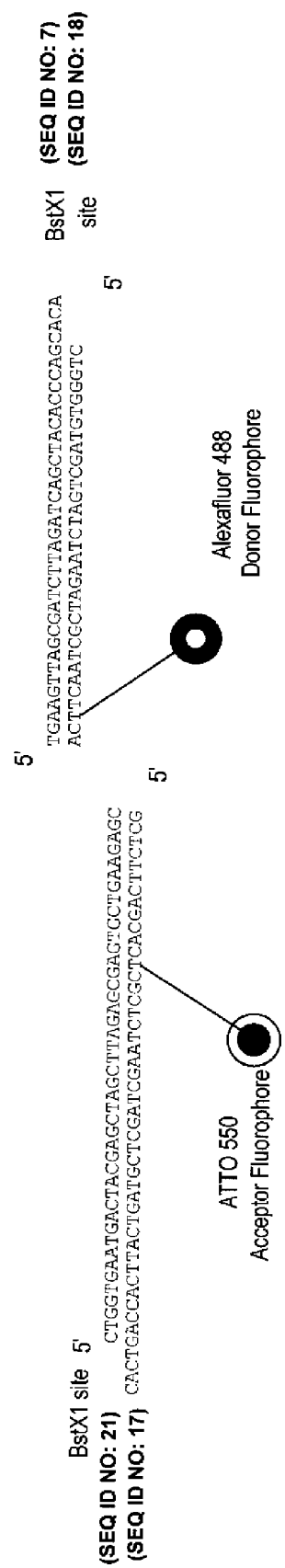
Fig. 19A
Fig. 19B

METHOD OF MEASURING THE AFFINITY OF BIOMOLECULES

This application is the National Phase filing of International Application No. PCT/GB2006/004208, filed Nov. 10, 2006, which claims priority to Great Britain Patent Application GB 0523366.3, filed Nov. 16, 2005, the disclosures of each of which are herein incorporated by reference.

FIELD OF THE INVENTION

This invention relates particularly, though not exclusively, to the field of analysis of biochemical pathways and to the interaction between biomolecules such as proteins and polypeptides.

BACKGROUND OF THE INVENTION

There has been an explosion of biological information in the last few years resulting from the use of high throughput experimental techniques. These techniques range from genome sequencing, microarray analysis, yeast 2-hybrid protein-protein interaction assays, to RNAi screens and the use of automated image analysis to study cell biological processes.

Following the successful implementation of each '-omic' technique, opportunities and bottlenecks are created at the interface between one set of techniques and the next. One key bottleneck is that of biochemistry.

Molecular machines, formed from complexes of proteins, are the building blocks underlying most cellular processes. Techniques such as the yeast 2-hybrid technique have been used to identify binary interactions between pairs of proteins on a genome-wide scale, while complementary analyses using complex purification and mass spectrometry are starting to identify the combinations of components that comprise each molecular machine. However, the detailed study of biochemical interactions requires the identification of affinity binding and rate constants, together with techniques for studying how these properties are physiologically regulated.

Standard 'test tube' biochemical techniques, including calorimetry and fluorescence anisotropy, require the time-consuming production and purification of microgram to milligram quantities of soluble proteins and are therefore unlikely to be scaled-up for high throughput applications. A potentially more promising technique, Surface Plasmon Resonance (Biacore®) requires somewhat less protein and can tolerate the presence of impurities (in some formats), but requires the careful timed flow of assay protein, followed by wash solutions over an immobilized binding partner and is therefore unlikely to be easily adapted for high throughput analyses. Typical protein requirements for Surface Plasmon Resonance and calorimetry are described below:

Isothermal Titration Calorimetry:

Measures: $K_d$, Stoichiometry (n), $\Delta G$, $\Delta N$
Requires: 1 ml of 10 μM solution; 20 nMoles; 1 mg of 50 KDa protein.

Surface Plasmon Resonance (Biacore®)

Measures: $K_{on}$, $K_{off}$, $K_d$
Requires: 2 mls of 100 nM solution; 200 pMoles; 10 μg of 50 KDa protein*.

*Calculation based on typical series of experiments required to establish a binding affinity in the ~10 nM range.

The high levels of proteins that are required in these assays result from the requirement to 'saturate' binding ligand concentrations 4-10× higher than the dissociation constant. This imposes the typical requirements shown in Table 1.

TABLE 1

| $K_d$ | 4 × $K_d$ | μg/ml for 50 KDa protein |
|---|---|---|
| 1 nM | 4 nM | 0.2 |
| 10 nM | 40 nM | 2 |
| 100 nM | 400 nM | 20 |
| 1 μM | 4 μM | 200 |

These levels of protein require time consuming and relatively expensive conventional protein synthesis and purification systems.

In vitro translation 'pull-down' experiments can be used to identify binding interactions between small amounts of radio-labelled protein produced in a translation extract (100-150 ng produced). However, like the yeast 2-hybrid technique, they suffer from the disadvantage that they are non-quantitative, they screen for picomolar to low nanomolar ranges of affinities and fail to screen for lower affinity interactions.

There is a requirement for new high-throughput biochemical techniques that are quantitative, sensitive, may use small volumes of analyte, may require a low number of moles of analyte, may achieve high (up to mid-micromolar typically about 1-5 pM to about 10-20 μM) concentrations and may be adaptable for massively parallel analyses.

SUMMARY OF THE INVENTION

According to one aspect of the invention there is provided a method of measuring the affinity of first and second biomolecules in which a first biomolecule is tethered by a first tether portion having a first tether portion length and a second biomolecule is tethered by a second tether portion having a second tether portion length, determining binding of adjacent first and second biomolecules to each other, varying at least one of the first and second tether portion lengths and determining binding of the first and second biomolecules.

The method of the invention is advantageous in that it allows very accurate control of the concentration of amounts of biomolecules and also in that it needs only very small amounts of the biomolecules—it allows equilibrium-binding studies to be carried out in pico- to attoliter volumes. The low volumes allow a range of concentration-dependent biochemical assays to be performed with very low input amounts of each biomolecule. By way of example, in a theoretical determination comparing a method in accordance with the invention with conventional techniques, conventional calorimetry would require 20 nanomoles of protein or 1 mg of protein of a 50 KDa protein; Surface Plasmon Resonance would require 200 picomoles of protein corresponding to 10 micrograms for a 50 KDa protein. In contrast, a comparable method in accordance with the invention would require only 10 attomoles and 50 picograms for a 50 KDa protein. Typically, nano- to zeptoliter, preferably pico- to attoliter, volumes of first and/or second biomolecules are used.

In this context, the term "biomolecule" includes both naturally-occurring molecules and synthetic molecules.

The first and second biomolecules may be tethered to a solid support such as a glass slide or microbead. In one such configuration, the first and second biomolecules are separately tethered to the same solid support. Alternatively, the first and second biomolecules may be tethered together in a "Y-shaped" arrangement. In another embodiment, the first and second biomolecules may be joined by a tether but not tethered to a solid support, in a "linear molecule" arrangement. For example, the first and second biomolecules may be tethered together and present in a solution.

Where the biomolecules are tethered to a solid support, the biomolecules may be randomly arranged over the solid support. Alternatively, the biomolecules may be tethered to discrete portions of, or areas defined on, the solid support such that the first and second biomolecules can only interact if they "stretch" to span the gap between the discrete portions. By controlling the distance between the discrete portions and/or the tether length, the proportion of bound and free biomolecules may be altered allowing the determination of affinity described above. Discrete portions of the surface may be coupled to the first and second biomolecules using a range of techniques including photo, electron or ion beam lithography to sequentially deprotect portions for coupling. Alternatively, direct etching/modification using atomic force microscope tips may be used to introduce selective regional surface modification. An advantage of this type of approach is that intermolecular distances may be directly controlled rather than relying on mean distances. In principle, this should allow for more accurate control of biomolecule concentration.

In a preferred embodiment where first and second biomolecules are tethered to a solid support, the method may be arranged to be operated in a nano-scale reaction zone. The formation of the reaction zone may be achieved by anchoring the tethers near each other so that at least some of the first and second biomolecules are closely adjacent to each other, such that the substantially hemispherical swept volumes defined by the free ends of each biomolecule overlap, allowing the first and second biomolecules to bind to each other. The volume of each hemispherical volume may be of the order of $2\times10^3$ to $1\times10^{12}$ nm$^3$. By varying the length of the tether portions, the effective concentrations of the biomolecules can be controlled allowing quantitative analyses.

The stiffness of the tethers is considered in terms of the persistence length (P) which is an experimentally measured parameter that characterises the stiffness as a single bending parameter of a flexible rod. (Bustamante, C., J. F. et al 1994. Science. 265:1599-1600; and Marko, J. F., and E. D. Siggia. 1995. Stretching DNA. Macromolecules. 28:8759-8770). In the case of relatively long tethers (P>approx five times less than the contour length of the tether) made of polymers such as DNA in solution, the tether can be represented by a worm-like chain model that is characterised by, the persistence length (P). Molecules much longer than the persistence length (P equals approx 50-90 nm for dsDNA) behave like random coils of a freely jointed chain with a segment length 2P and a Gaussian distribution of segment density.

In addition to varying the length of the tethers, the inter-anchor distance can be altered to vary the overlap of the swept volumes. This method can be used to alter the stoichiometry of tethered molecules and to fully exploit the special case when long flexible tethers are used.

Computer simulations (Monte Carlo) have been used to calculate the probabilities of free DNA end distribution (for example, see Jian and Vologodskii (1997). A combined wormlike-chain and bead model for dynamic simulations of long linear DNA, J. Comp. Physics 136 pp 168-179.).

The probability distribution of the free end of a tether in the nanotether context is determined by a number of factors including the stiffness of the tether, the temperature and the ionic conditions. By using long tethers in proportion to the persistence length (e.g. greater than 5 times P), the inter-anchor distance can be varied to probe the effective concentration gradient within the substantially hemispherical swept volume.

In this concentration gradient, the lowest concentration would be closest to the surface swept by the tether at its full contour length (stretched straight). The concentration would then increase to a maximum close to the average centre of mass due to entropic considerations. The probability that two tethered biomolecules will interact at a particular inter-anchor distance will thus be dependent on the calculated probability distribution and will increase as the inter-anchor distance decreases. Approaches to alter the probability distribution of flexible tethers within their swept volumes (e.g. inducing bulk liquid flow or the use of vibrating supports) may be used to enhance the utility of tethers far beyond their persistence lengths (e.g. 20-40 times P).

By measuring the interaction distributions of a range of 'test case' biomolecule interactions (e.g. GSK-3 and Axin peptide; streptavidin—biotin; antibody—antigen), it will be possible to correlate the probability distribution with the inter-anchor distance and to equate this directly to an affinity binding constant. Alternatively mathematical models of this process can also be produced based on the studies of Jian (supra).

Both varying tether length and inter-anchor distance are proposed as methods for varying tethered biomolecule concentrations. At high length: P values, the probability distribution may be the most effective method of calculating affinity. In a linear molecule or Y-shaped molecule embodiment, the first and second tether portion length may be varied to vary the biomolecule concentrations.

Techniques that measure the proportion of the first and second biomolecules that are molecularly close to each other can be used to quantify the proportion of interacting first and second biomolecules. For example, the proportion of first and second biomolecules that are molecularly close to each other can be determined by Forster resonance energy transfer (FRET).

In a preferred method, the assay readout is the intensity of FRET between fluorophores coupled to the head oligonucleotides attached to the first and second biomolecules. A laser, appropriate to the excitation maximum for a fluorophore attached to the first biomolecule, is used to excite that fluorophore. Emission at the wavelength maximum from a fluorophore attached to the second biomolecule is recorded to assess the level of FRET. In practice, for FRET to occur, an excited molecule of the first fluorophore has to be molecularly close (<10 nm) to the second fluorophore for energy to be transferred, leading to emission at the characteristic wavelength of the second fluorophore. This will occur when the first and second biomolecules are also molecularly close due to the formation of the first biomolecule/second biomolecule complexes. In a preferred variant of the FRET technique, fluorescence lifetime measurement (FRET/FLIM) is used to measure the time dependence of FRET since this technique offers improved sensitivity ('Fluorescence Lifetime Imaging: An emerging technique in Fluorescence Microscopy', C. G. Morgan, Chromosome Research, 4(4), 261-263, 1996.). Appropriate controls (e.g. spots of the first and second biomolecules alone) will be used to normalise signal levels.

In a preferred embodiment, FRET may be measured using a lens to focus the lasers on glass slides containing arrays of tethered biomolecules. In other embodiments, purpose-built machines are arranged to overcome the limitations that confocal microscopes have due to their design for other purposes. In particular, the use of photomultipliers and cooled charge-coupled devices (CCDs) may enhance the sensitivity of detection of the low level FRET signals, potentially leading to the detection of FRET between tethered pairs of single first and second biomolecules (for example, see Walter et al., Biopolymers (Nucleic Acid Sciences), Vol. 61, 224-241 (2002)). Alternatively, Total Internal Reflection Fluorescence Microscopy (TIRF) may be used (Surface fluorescence microscopy with evanescent illumination, Axelrod, D., Light Microscopy in Biology, Lacey, A. (ed), Oxford University Press, New York, 399-423 (1999)).

In an alternative solution, nanoscale spheres or "quantum dots", nanocrystals which absorb light but quickly re-emit the light in a different colour, may be tethered in place of the single fluorophores. These conjugates may offer higher FRET efficiencies due to the increased number of fluorescent molecules. Alternatively, the nanoscale spheres would allow fluorescence correlation spectroscopy to be performed using a high-resolution light confocal microscope. For tethers longer than 2 Kb (0.6 µM), the formation of first biomolecule/second biomolecule complexes may be directly recorded due to the proportion of fluorescent dot pairs in proportion to those that show some separation.

The first and/or second tethers, or a single tether in the case of a linear molecule, may be formed from nucleotides. Preferably, a tether is generated from double stranded DNA (dsDNA). Alternatively, a tether may be made from other polymers such as carbon nanotubes (D. H. Jung et al Covalent attachment and hybridization of DNA oligonucleotides on patterned single-walled carbon nanotube films. Langmuir. 2004 Sep. 28; 20(20):8886-91.), amyloid fibrils, or DNA crossover complexes for example DX hybrids, which include an even number (typically 4, 6, or 8) strands of DNA and are somewhat stiffer than dsDNA; *J. Am. Chem. Soc.* (2000), 122, 1848-1860, Construction, Analysis, Ligation, and Self-Assembly of DNA Triple Crossover Complexes). Furthermore, the 'stiffness' or persistence length (P) and electrostatic charge of tethers such as dsDNA may be modulated by chemical modification, interchelation with molecules such as ethidium bromide or other suitable interchelating agents, which are typically organic compounds to allow insertion between the dsDNA bases or are positively charged and polymeric to complex with DNA based on affinity for the negatively charged phosphate backbone of DNA. The stiffness of DNA may also be altered by complexing with DNA binding proteins along the length of the tether. The stiffness of other tethers may be modulated by other means. For example, the stiffness of tethers comprising DX hybrids may be modulated by varying the number of strands; for tethers comprising carbon nanotubes by increasing the number of concentric tubes forming each nanotube.

In a preferred embodiment, variable-length dsDNA tether portions are ligated together to form a tether. For example, a tether body portion may be linked to head and tail tether portions to produce the tether. The nucleotides of the body portion may be ligated to head and tail portions in solution.

For non-nucleotide tethers, chemical cross-linking methods can be used to attach head and tail oligonucleotide linkers to the respective ends of the body portions of the tethers.

Where the tethers comprise nucleotides, the or each tether portion length may typically be of the order of 50 basepairs (bp) to 50 Kb preferably, 200 base pairs to 20 kbase pairs, or 30 to 12 000 nm, preferably 60 to 6000 nm, for other tethers.

The tethers may be tethered to a surface by means of anchors. The anchors may be single-stranded amino-modified oligonucleotides. The tethers (head, body and tail) can then be hybridised to a solid support to which anchor oligonucleotides have been immobilised. The solid support may be a modified glass substrate. Standard techniques may be used to covalently couple an anchor oligonucleotide (for example, see: Chrisey, L. A., Lee, G. U., and O'Ferrall, E. (1996) Covalent attachment of synthetic DNA to self-assembled monolayer films *Nucleic Acids Res.* 24:3031-3039). A preferred method involves coupling amino-modified anchor oligonucleotides to a glass support treated with an agent such as amino silane and p-phenylene1,4 diisothiocyanate (PDC). Other substrates that can be modified to bind a tether to a surface are also contemplated, including agarose and sepharose.

In one embodiment, the format of the support is a glass slide onto which oligonucleotide anchors or tethers are printed in arrays of spots using commercially available split pin arraying machines such as those available from Genetix. More specialist solid supports, based on miniaturisation techniques derived from microelectronics, may be used in more sophisticated implementations that are designed to further miniaturise the analysis and to integrate better with readout systems.

In an alternative format, the support may be provided by microbeads that are coupled in formats that generate a unique relationship between a single bead and tether combination. This format enables the adaptation of the technology to microfluidic systems, and may enhance probe density particularly where relatively long tethers, say about 50 µm, are used to test for high affinity interactions at high inter-anchor distances. Suitable microbeads may include polystyrene, coated ferrous/ferric particles, gold particles, sepharose, agarose, glass or carbon.

In an arrayed-spot implementation, amino-terminal oligonucleotide anchors for the first and second biomolecules may be covalently coupled to the modified glass substrate. A range of other approaches can be used to vary the inter-tether distance. In one implementation, the distance between the oligonucleotide anchors is increased by the use of a non-specific amino terminal oligonucleotide (which is designed not to bind to other tether components) that is titrated into the specific oligonucleotide mix. The greater the proportion of the non-specific oligonucleotide; the greater the resulting distance between specific oligonucleotide anchor. Alternatively, the proportion of modified silane molecules may be reduced prior to oligonucleotide coupling. Inter-anchor mean distances may be varied from distances greater than the tether length to the maximal oligonucleotide tether capacity. The maximal coupling density possible using published protocols (e.g. Chrisey et al 1996 supra) is 20 pmoles of bound DNA/$cm^2$ which equates to an mean inter-anchor spacing of 1.6 nm; Chrisey, L. A., et al (1996) supra. This inter-anchor density massively exceeds that required for the most probable range of anchor densities which would normally range from about 5 nm to about 1 µm.

In the above implementation, the non-specific amino-specific oligonucleotide functions to cap the reactive groups and will also make the surface of the support electrostatically negative, thereby minimizing the association of the negatively-charged DNA tether with the surface. Alternatively, hydrophobic lipid groups may be coupled to the glass surface to discourage DNA-surface association due to the incompatibility of hydrophobic—hydrophilic associations. For example, suitable lipid groups may include phosphatidyl ethanolamine.

In an alternative implementation, the sequences present in adjacent anchor oligonucleotides are synthesized in series (i.e. as a single oligonucleotide). This effectively generates a common anchor for both the first and second tethers and ensures that the swept volumes entirely overlap. There may be advantages to this approach if the binding of very low numbers (as low as 1 pair) of biomolecules were to be studied. In a variant of this implementation, where the first and second biomolecules are not tethered to a separate solid surface, the first and second biomolecules may be tethered at the respective ends of a single tether and measurements could be made in solution.

In a preferred method of connecting protein biomolecules to nucleic acid tethers, protein nucleic acid conjugates are produced according to the method described in: Jung, G. Y., and Stephanopoulos, G. (2004) A functional protein chip for pathway optimization and in vitro metabolic engineering Science 304, 428-431. This description is in turn based on the original method described in: Roberts, R. W., and Szostak, J. W. (1997) RNA-peptide fusions for the in vitro selection of peptides and proteins Proc. Natl. Acad. Sci. U.S.A 94, 12297-12302. In short, the method involves the use of an in vitro translation reaction to covalently attach a nascent peptide by its C-terminus close to the 3' end of an mRNA-DNA conjugate. An additional class of methods for connecting protein biomolecules to nucleic acid tethers that can be used with equal preference to the method described above. These methods generically involve the synthesis of a fusion protein comprising the biomolecule of interest attached to a modified enzyme (shown schematically in the accompanying FIG. 23; species A fused to species X). This type of system has been described for three different enzymes, the Halo-Tag, the AGT tag and cutinase (Hodneland, et al., (2002) Selective immobilization of proteins to self-assembled monolayers presenting active site-directed capture ligands. Proc Natl Acad Sci USA 99, 5048-5052; Keppler et al., (2004a) Labeling of fusion proteins of O6-alkylguanine-DNA alkyltransferase with small molecules in vivo and in vitro. Methods 32, 437-444; Keppler et al., (2004b) Labeling of fusion proteins with synthetic fluorophores in live cells. Proc Natl Acad Sci USA 101, 9955-9959; Temple et al., (2006). From genome to proteome: developing expression clone resources for the human genome. Hum Mol Genet 15 Spec No 1, R31-43). Following synthesis, the fusion enzyme (X) is irreversibly and covalently coupled to a chemically synthesised substrate. In the systems described, a wide range of modified substrates have been generated. In the implementation proposed, a Head Set oligonucleotide is chemically synthesised that incorporates the substrate species (FIG. 23; Y). This synthesis of the covalently coupled oligonucleotide could also incorporate the Donor or Acceptor Fluorophore allowing a 1-step coupling and labelling protocol.

There are three main advantages to the use of the approach described in Jung and Stephanopoulos (2004) supra in the context of the present invention. First, the protein-nucleic acid complex can be purified away from in vitro translation extract proteins, following annealing to the immobilised tethers and washing. Second, multiple messenger RNAs can be simultaneously translated and conjugated to their unique coding nucleic acids; this enables high throughput approaches to be taken to protein production. Third, the proteins produced in the in vitro translation extracts (~150 ng/translation) are in a large excess over that required to saturate a typical 100 μm diameter microarray spot of tethers (~8 pg of a 50 KDa protein in a spot containing 30 nm inter-anchor distance with $1 \times 10^7$ molecules). Jung and Stephanoupoulos (2004) showed that the density of 'oligonucleotide anchors' in their approach was the primary determinant of the levels of immobilized nucleic acid-protein complexes. In an entirely analogous fashion, the proportion of tethers used in a method in accordance with the invention will determine the proportions of tethered first and second nucleic acid-protein complexes.

Alternative methods of making protein-nucleic acid conjugates may be used, including the direct chemical crosslinking of purified protein biomolecules to modified oligonucleotides. As an alternative, protein-nucleic acid complexes may be generated in situ by annealing the mRNA-DNA conjugate to the immobilized tether first and translating the messenger RNA, whilst bound to the tether, by adding in vitro translation extracts to the tethered messenger RNA.

Alternatively, messenger RNA may be designed to generate protein fusions between the protein biomolecules of interest and a second protein domain X. The second domain X may be designed to have a very high affinity for an engineered component of the head oligonucleotide or the head end of the tether. For example, if the X domain is a high affinity specific DNA binding protein (e.g. lambda repressor), its cognate DNA site may be introduced into the head oligonucleotide complex to enable the nascent protein to associate with the tether via the DNA binding moiety. Alternatively, X could be a molecule such as streptavidin and a corresponding binding partner—in this case biotin—would be chemically coupled to the head oligonucleotide.

Typical protein biomolecules include enzymes, antibodies and receptors. In further alternative methods, the first and/or second biomolecule may be a bioactive molecule other than a protein. The only requirement is that the alternative biomolecule is capable of maintaining its functional activity whilst being coupled to a tether. Alternative molecules include peptides, peptide analogues, such as synthetic amino acids, combinatorial polymer libraries, small molecules (say <1000 Daltons, for example chemically-synthesized drugs), polysaccharides, and catalytically active RNA species.

In a preferred method, nucleic acid protein conjugates are annealed through complimentary sequences, provided by either of the first and second biomolecules, close to the 3' end of the nucleic acid component to complementary sequences in a head oligonucleotide tether portion. This concentrates the nucleic acid conjugates from molarities typical of in vitro translations (e.g. 10 nM) to the experimental concentrations.

Simple well-characterised equilibrium binding equations (Michaelis Menten) can be used to derive molecular interaction parameters based on the concentrations of the first and second biomolecules and the proportion of first biomolecule/second biomolecule bound.

For example, in a typical experiment to accurately determine the $K_d$ of an interaction between first and second biomolecules which are tethered to a support, first and second biomolecules having a range of tether lengths and inter-anchor distances is set up as an array of spots using appropriate combinations of anchors and tethers for the first and second biomolecules. This generates a standard range of concentrations. These concentrations are first plotted against the proportion of bound first/second biomolecule complex and the concentration of the first biomolecule (or the second biomolecule) required for half maximal binding is determined (this concentration is the $K_d$).

According to a further aspect of the invention there is therefore provided a method of determining the $K_d$ of an interaction between first and second biomolecules by determining the proportion of bound first and second biomolecules for a range of concentrations of the first and second biomolecules and the determining the concentration of the first or second biomolecule required for half maximal binding of the first and second biomolecules—the $K_d$. The affinity of a first biomolecule to a library of second biomolecules may be determined. The library of biomolecules may comprise at least a significant portion of a transcriptome or proteome.

Methods in accordance with the invention offer the potential of screening interactions between a single biomolecule A and a library of molecules B1, B2, B3 ... $B_n$. In one format, each spot is occupied by only biomolecule A and B1 or A and B2 ... A and $B_n$. In a preferred implementation for protein molecules, head tether portions recognising unique (for example coding) regions from the 3' end of messages B1, B2, B3 ... $B_n$ are generated and coupled to the core tethers as described earlier. $B_n$ may be libraries of proteins potentially representing a transcriptome/proteome. Alternatively, $B_n$ may be libraries of peptides used for defining interaction sites. Alternatively, $B_n$ may be tethered libraries of chemical compounds ranging from small molecule compounds to libraries of synthetic polymers.

By using an anchor/tether for the second biomolecule that can be cleaved together with initial saturating concentrations of the first and second biomolecules, it is possible to determine $K_{off}$. In this scheme, the rate of decay of first biomolecule/second biomolecule complex levels is monitored in real time following cleavage of the tether for the second biomolecule. This type of analysis is analogous to that used in surface plasmon resonance to determine the $K_{off}$.

The effect of a third, tethered or non-tethered biomolecule on the interaction between the tethered first and second biomolecules may also be studied.

According to a further aspect of the invention there is provided a method in which the $K_{off}$ value for an interaction between the first and second biomolecules is determined by providing initial saturating concentrations of the first and second biomolecules, cleaving a second biomolecule tether portion or anchor and monitoring any change in levels of bound first and second biomolecules.

According to a further aspect of the invention there is provided a method of determining the change in free energy ($\Delta G°$) value for an interaction between a first and second biomolecules, the method comprising determining the proportion of bound biomolecules at a first temperature and determining the proportion of bound biomolecules at a second temperature and comparing the proportion of bound biomolecules at the respective first and second temperatures. Typically, the temperature of the biomolecules may be varied by altering the temperature of the experimental apparatus used to perform the method.

According to another aspect of the invention there is provided apparatus for determining the affinity of first and second biomolecules, the apparatus comprising a first biomolecule tethered by a first tether having a first tether length, a second biomolecule tethered by a second tether having a second tether length, means for determining binding of adjacent first and second biomolecules to each other, and means for varying at least one of the first, and second tether lengths.

At least one of the first and second biomolecules may be tethered to a surface of the apparatus. Preferably, both the first and second biomolecules are tethered to a surface. The biomolecules may be tethered separately to the surface or together in, for example, a Y-shaped or linear arrangement. Alternatively, the biomolecules may be tethered together and associated with the apparatus in the form of a solution.

The surface may be provided by a solid support. Preferably, the solid support is a glass slide. Alternatively, the solid support may be a micro bead.

Other aspects of the apparatus may be provided by preferred method features described above.

BRIEF DESCRIPTION OF THE DRAWINGS

Methods and apparatus in accordance with the invention will now be described, by way of example, with reference to the further accompanying FIGS. 1 to 22 in which:

FIG. 10 illustrates a method in accordance with the invention;

FIG. 11 illustrates the use of a method in accordance with the invention to measure $K_{off}$;

FIG. 12 is a scheme showing operation of a linear molecule arrangement of biomolecules in accordance with the invention in which:

Figure 12:
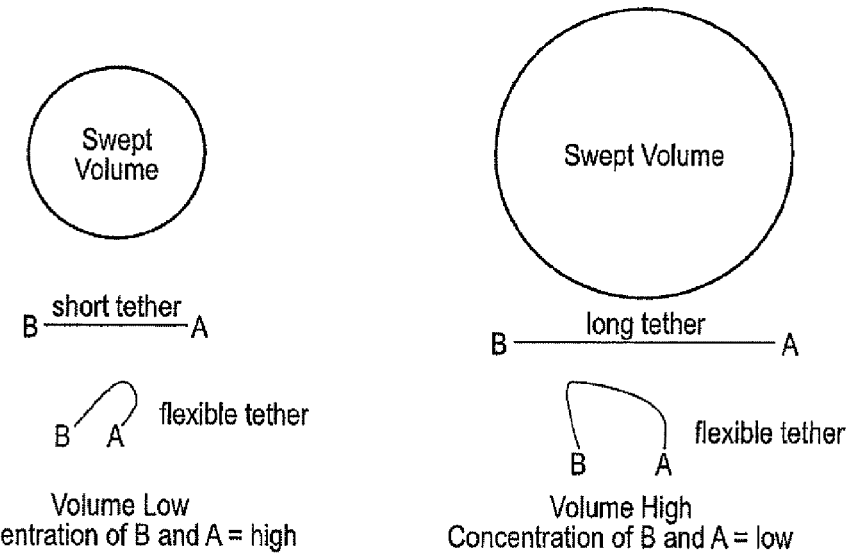
Figure 12:
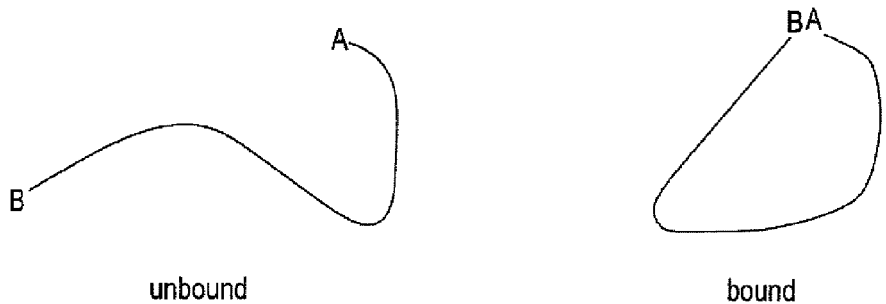
Figure 12:
Figure 13:
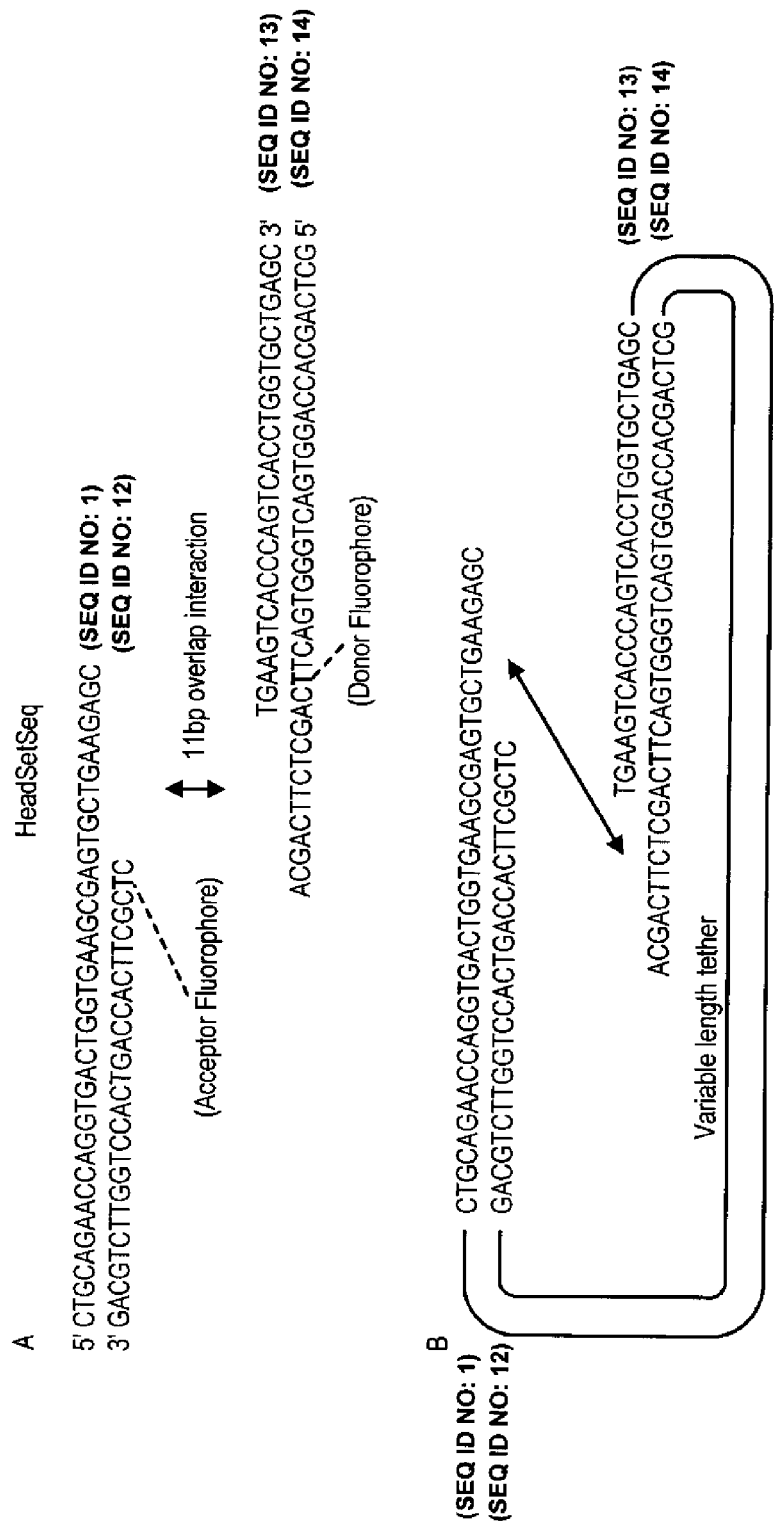

A. is an illustration of spheres swept by the free ends of short and long flexible tethers;

B. is an illustration of a possible conformation of free and bound variants of a linear molecule representing an intra-molecular interaction between biomolecules A and B;

C. is an illustration of free and bound variants undergoing inter-molecular interactions between A and B;

FIG. 13 is a diagram showing 'head-set' oligonucleotides used for forming tethers in which:

A. shows separate molecules of the form shown in FIG. 12C;

B. shows a linear molecule with acceptor and donor head sets attached.

Figure 14:
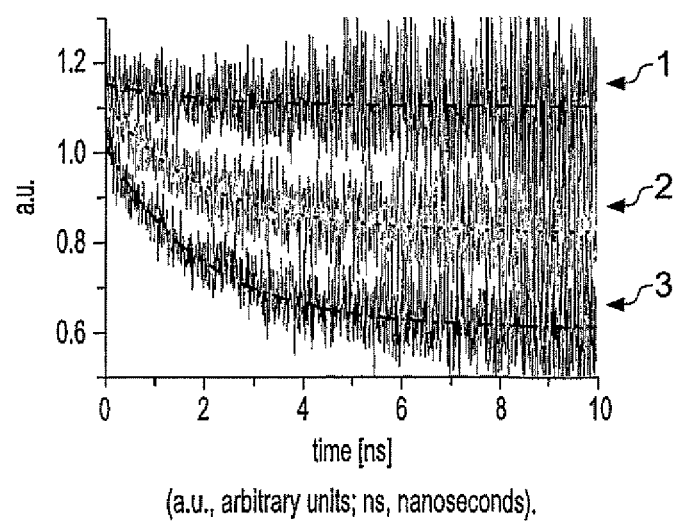
Figure 15:
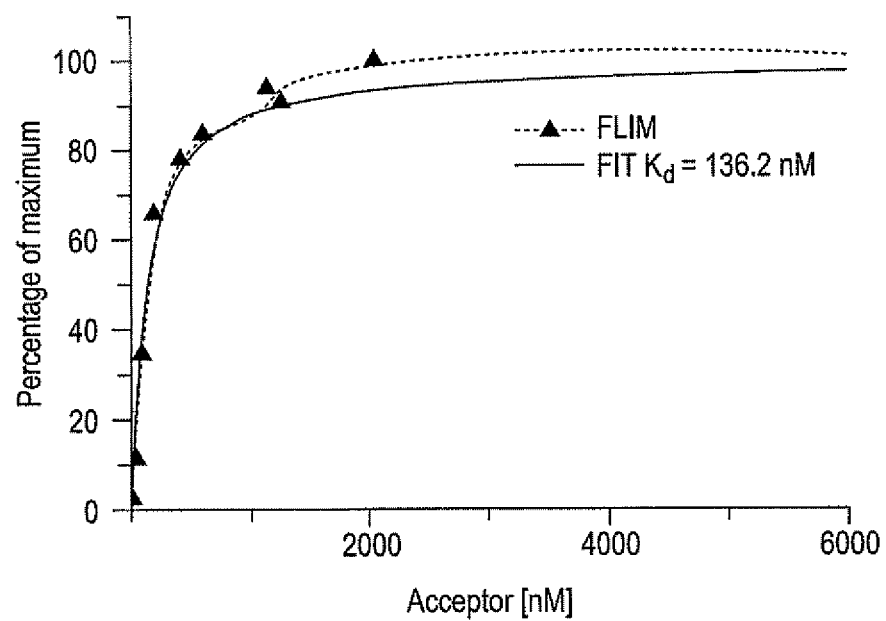
Figure 16:
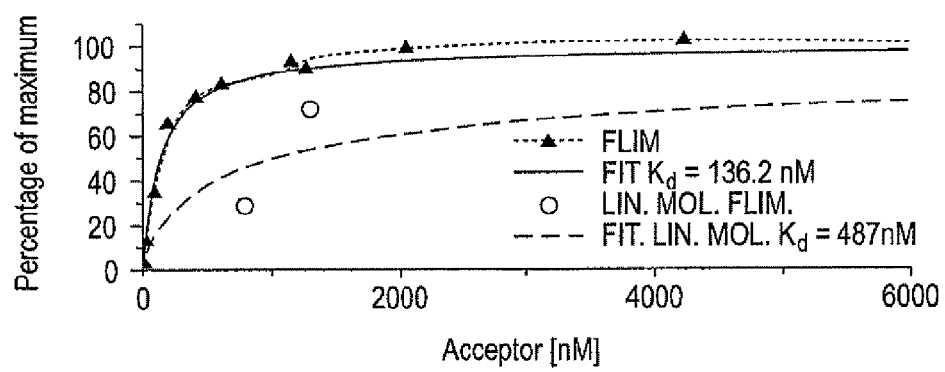
Figure 17:
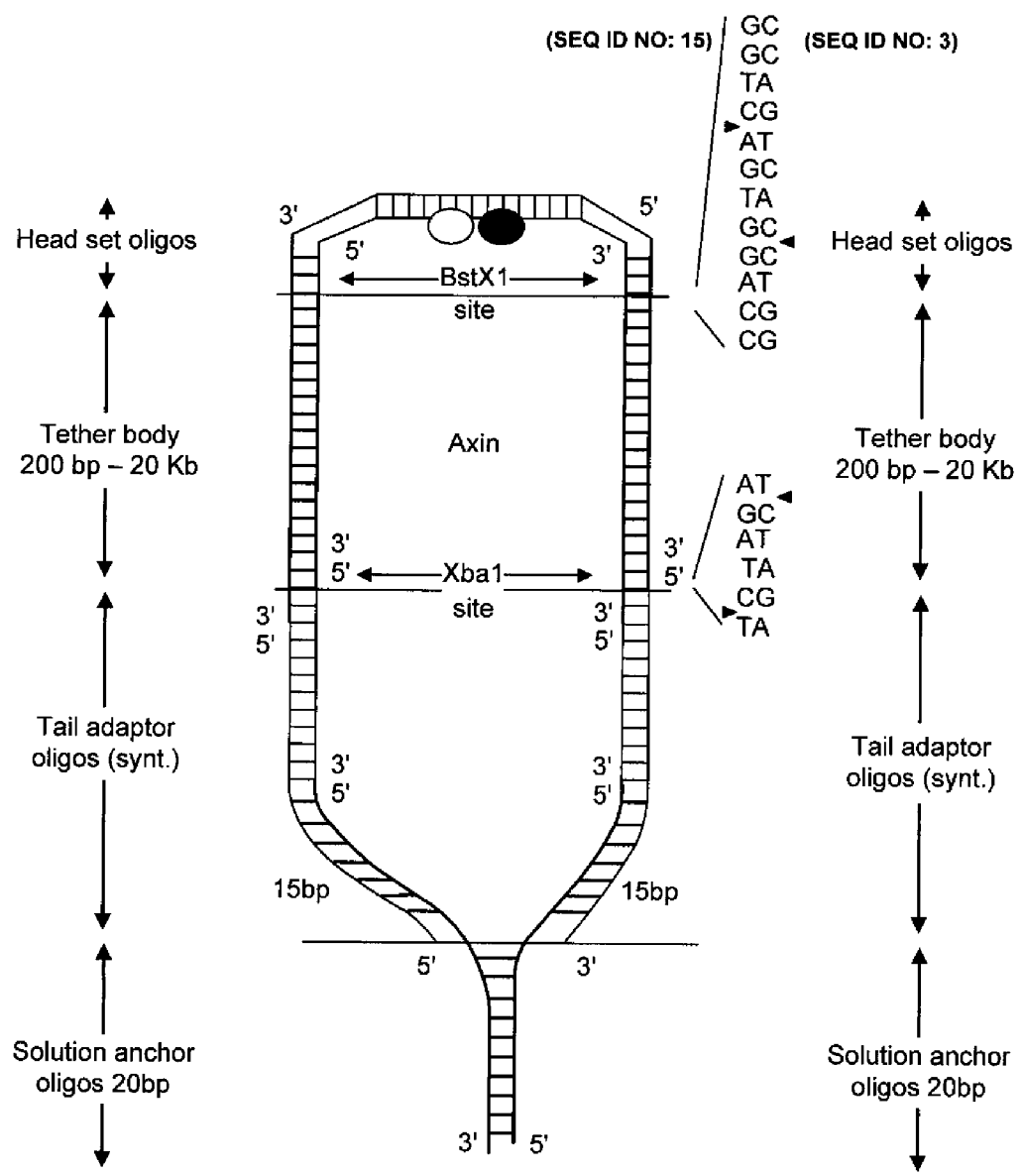
Figure 18:
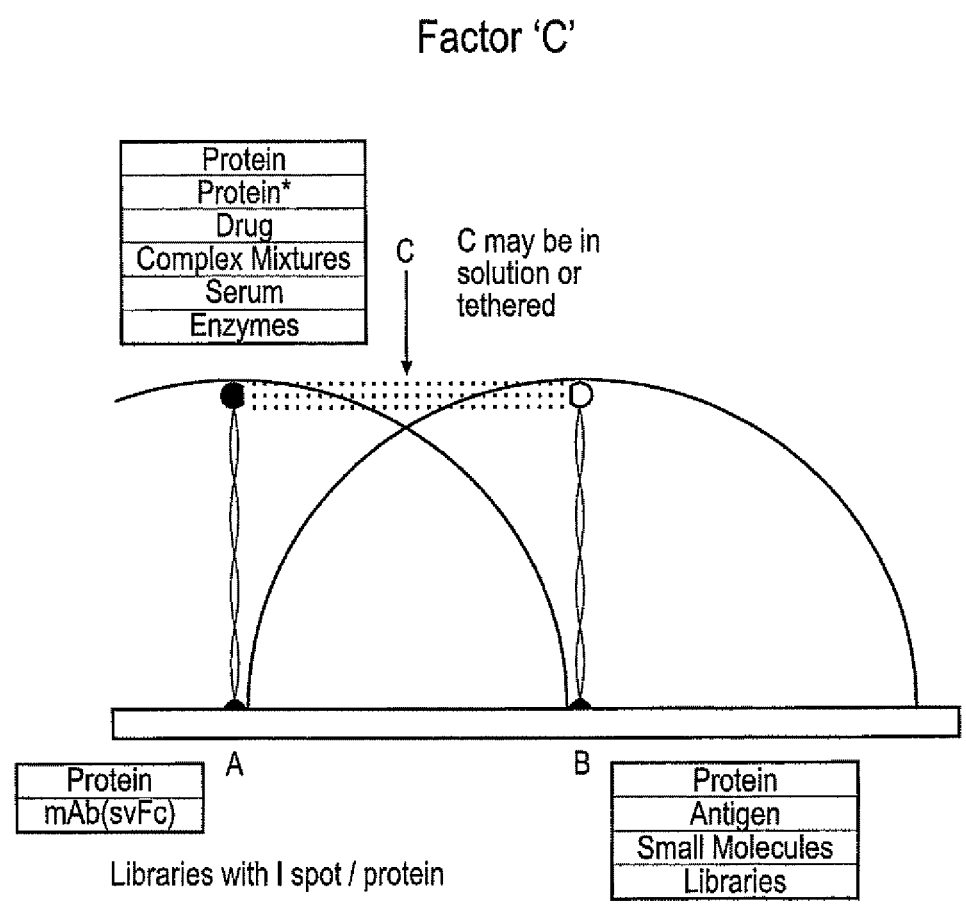
Figure 20:
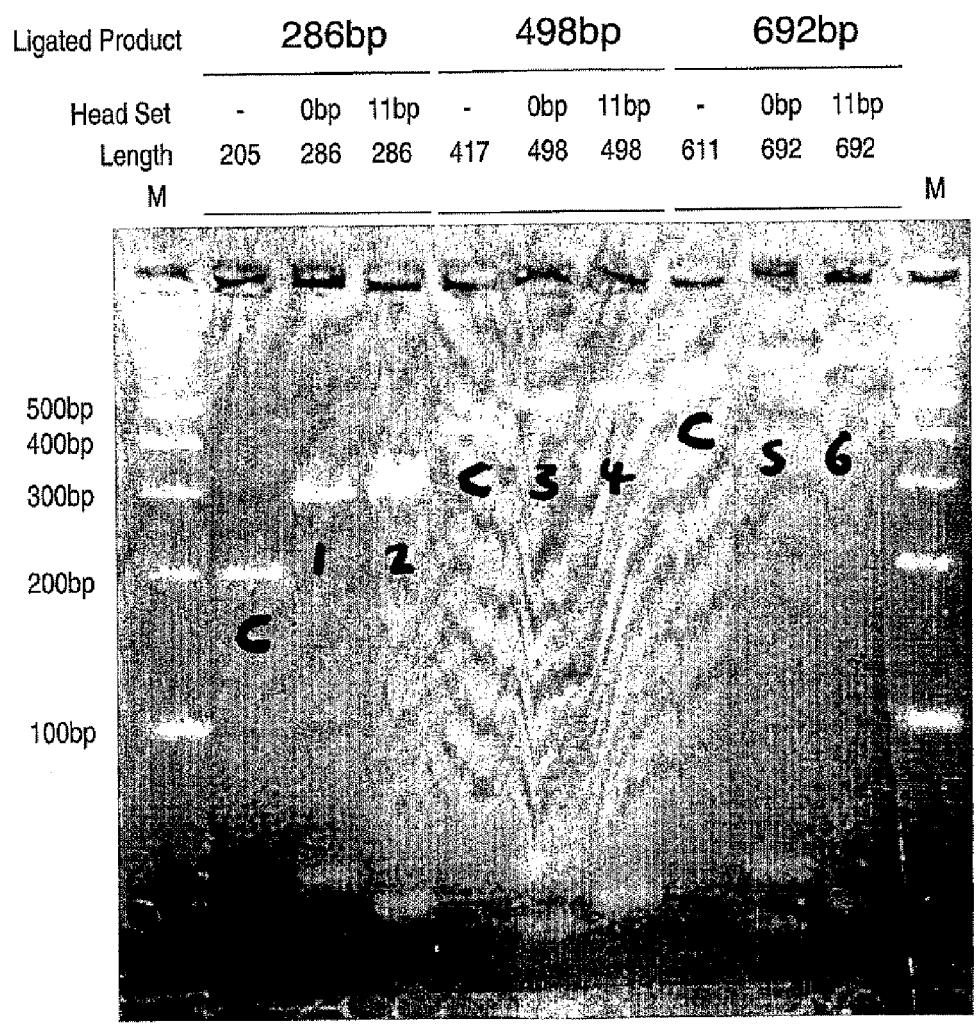
Figure 21A:
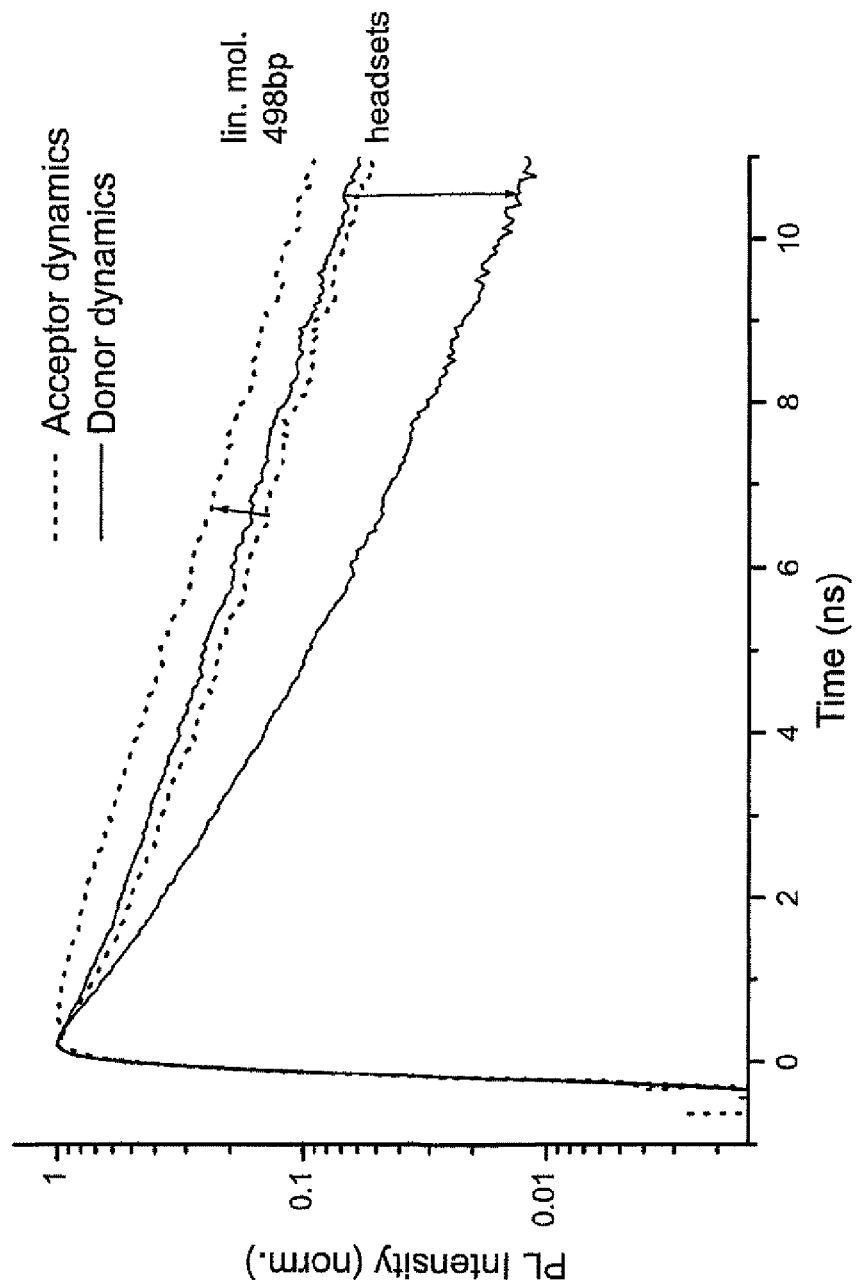
Figure 21B:
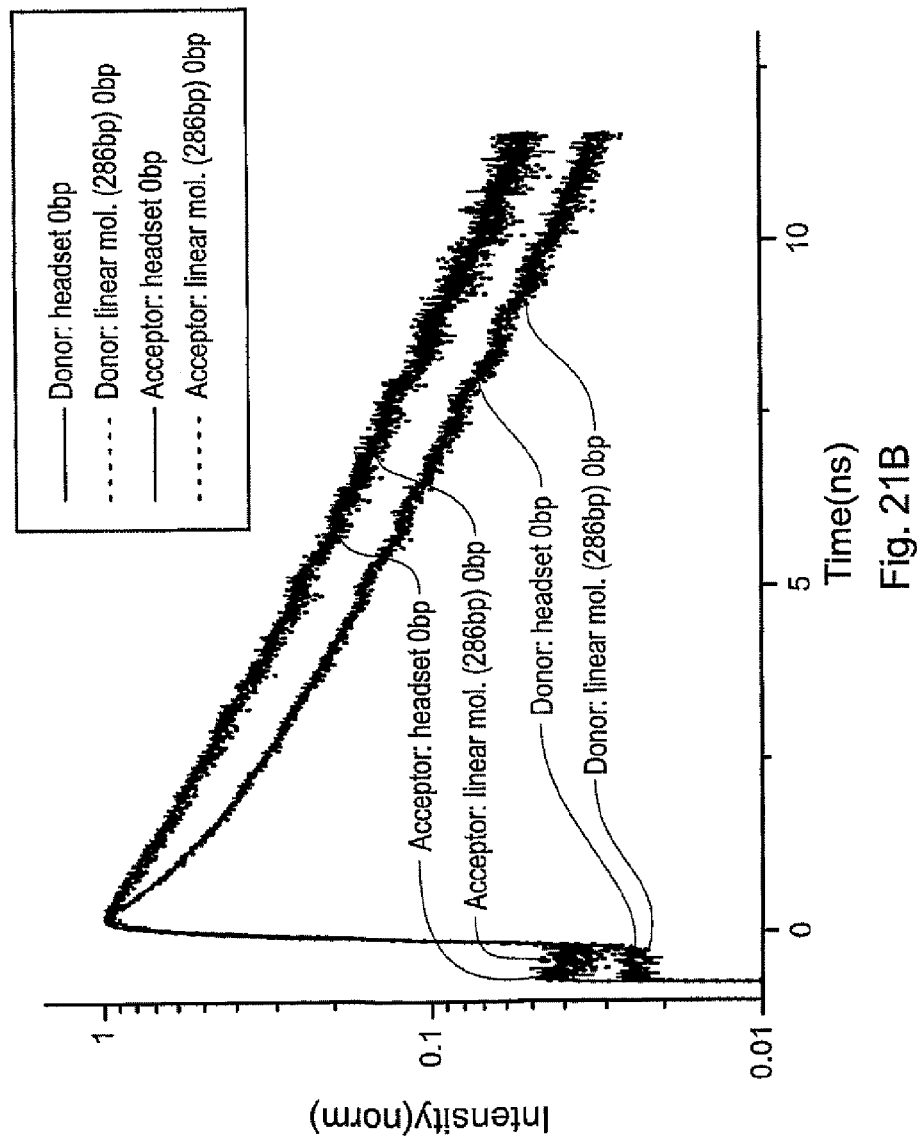
Figure 22:
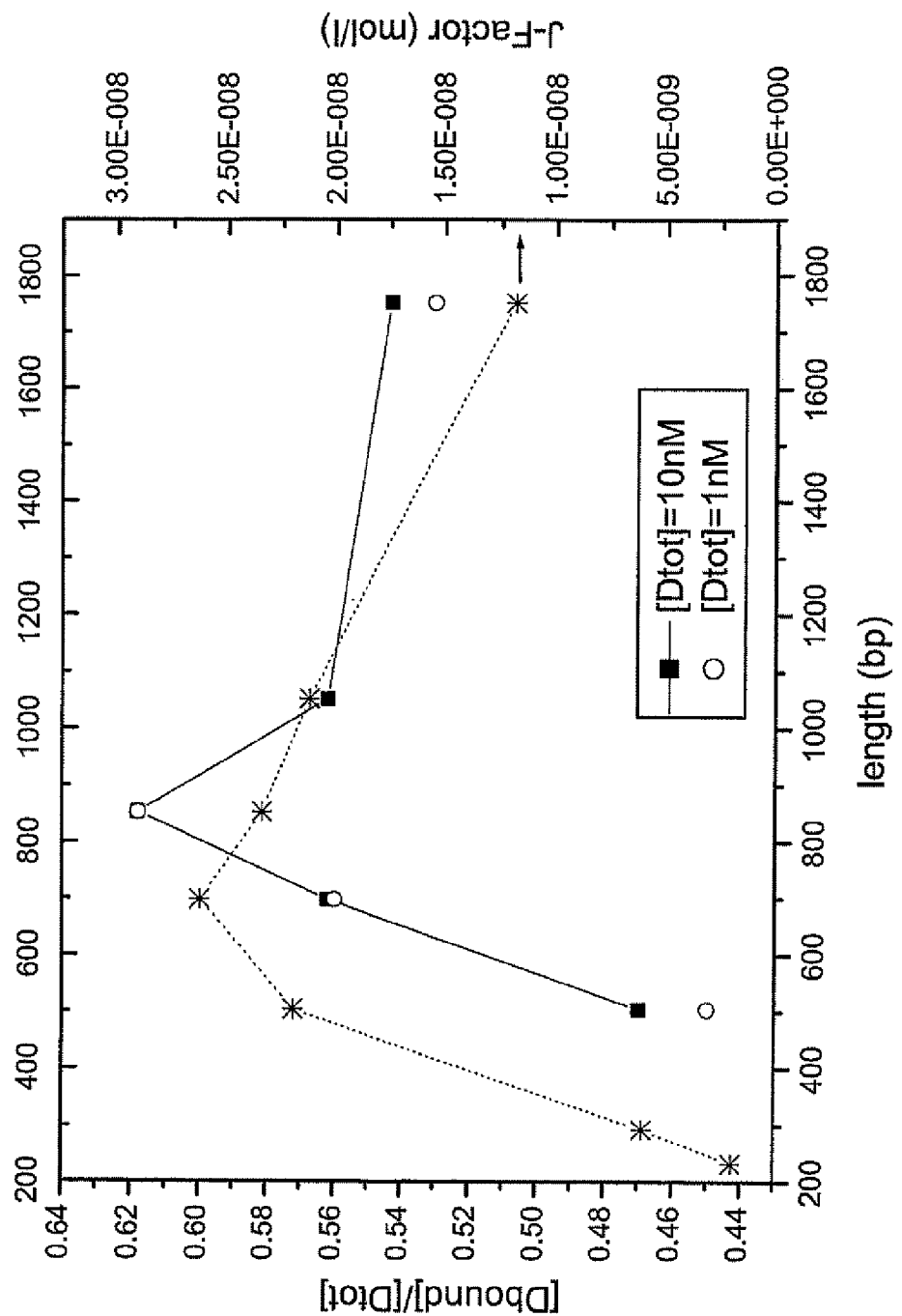

This molecule takes the form shown in FIG. 12B;

FIG. 14 shows time dependent decay of donor fluorescence due to FRET;

FIG. 15 is a graph illustrating an Acceptor Head-Set Titration;

FIG. 16 illustrates experimental measures of linear molecule affinity for:

a. a range of lengths; and b. a range of concentrations;

FIG. 17 illustrates a Y-shaped molecule in accordance with the invention;

FIG. 18 illustrates a determination of Factor 'C' using a method in accordance with the invention as described below;

FIG. 19 illustrates the design of biomolecules formed by oligonucleotides;

FIG. 20 is a photograph of a gel analysis of biomolecules having various length tether portions;

FIG. 21 shows results of FRET experiments using the oligonucleotides of FIG. 19; and FIG. 22 is a graph illustrating the variation of the proportion of bond molecules with the length of DNA tethers.

Figure 23:
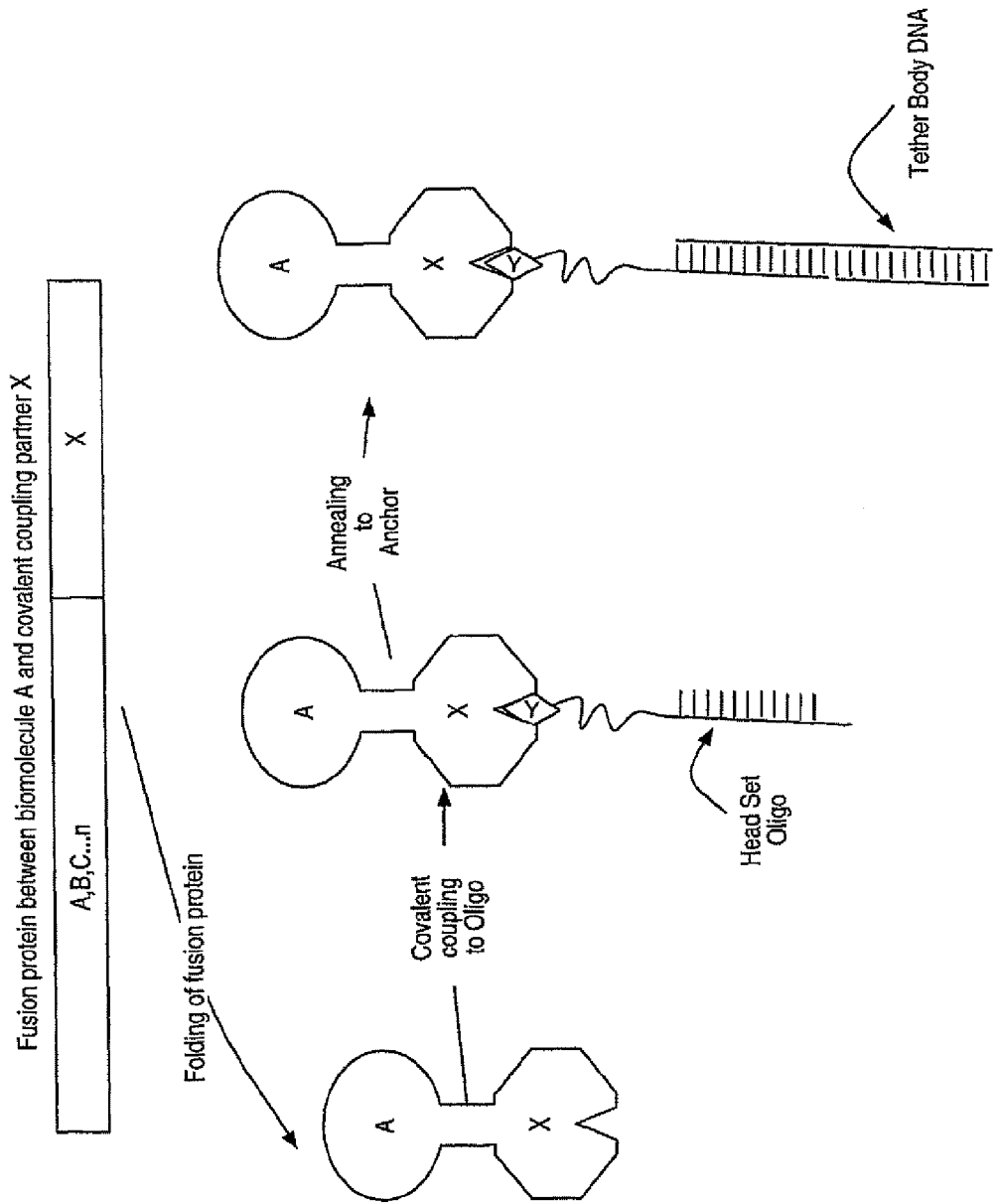

FIG. 23 shows a schematic of a fusion protein comprising a biomolecule of interest attached to a modified enzyme coupled to an oligonucleotide.

1 OVERVIEW OF A METHOD IN ACCORDANCE WITH THE INVENTION

Figure 1:
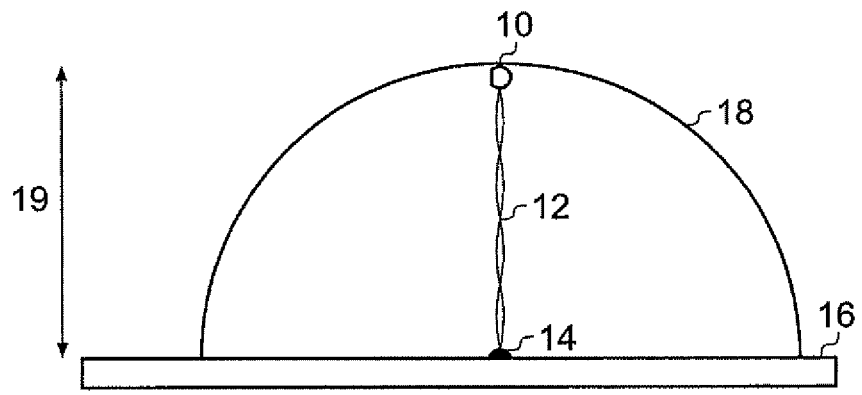
FIG. 1 is a diagram showing a tethered biomolecule for use in a method of the invention.

FIG. 1 shows a single first biomolecule 10 tethered by a first tether 12 through anchor 14 to surface 16. The first biomolecule 10 is free to move on the tether 12 about anchor 14 in a substantially hemispherical volume 18. The volume of volume 18 is determined by the first tether length 19.

Figure 2:
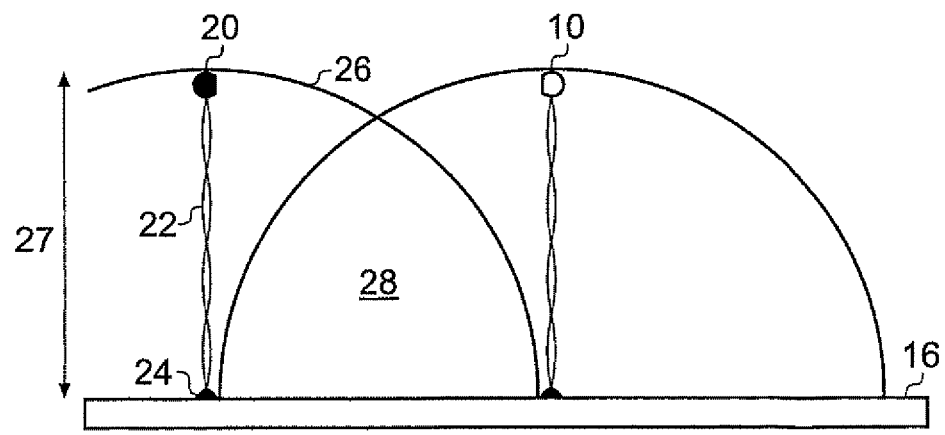
FIG. 2 is a diagram showing two tethered biomolecules for use in a method of the invention.

FIG. 2 shows anchored first and second biomolecules 10 and 20. The second biomolecule 20 is tethered by a second tether 22 via an anchor 24 and is also free to move in a substantially hemispherical volume 26. The volume of volume 26 is determined by the second tether length 27. The hemispherical volumes 18 and 26 overlap to define a reaction zone 28.

Figure 3A:
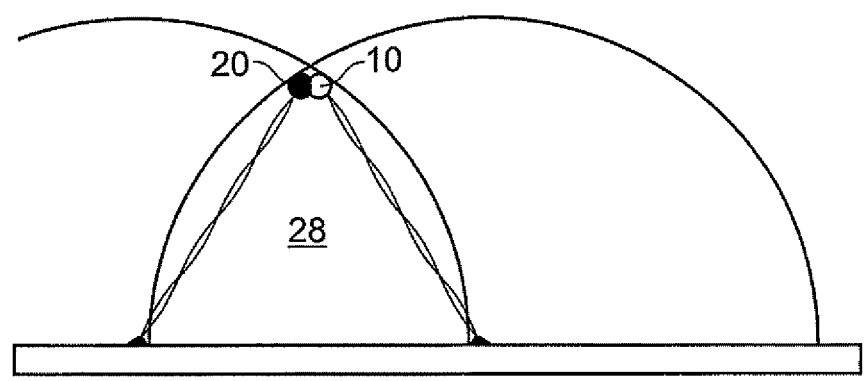
FIG. 3A is a diagram showing the biomolecules of FIG. 2 binding.
Figure 3B:
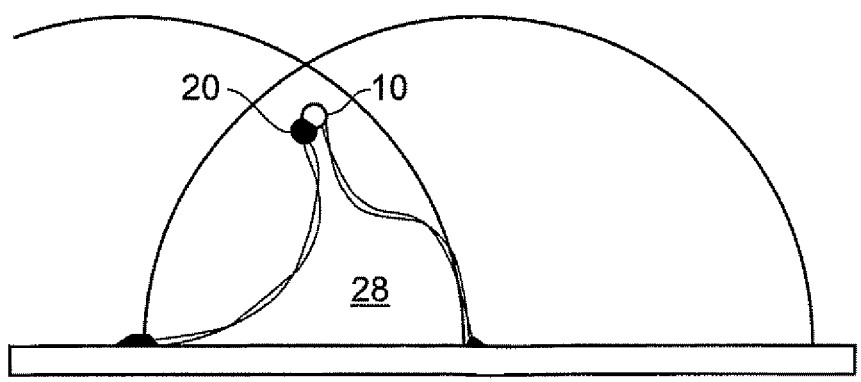
FIG. 3B illustrates the biomolecules of FIG. 3A binding and illustrates the flexible nature of the tethers.
Figure 4A:
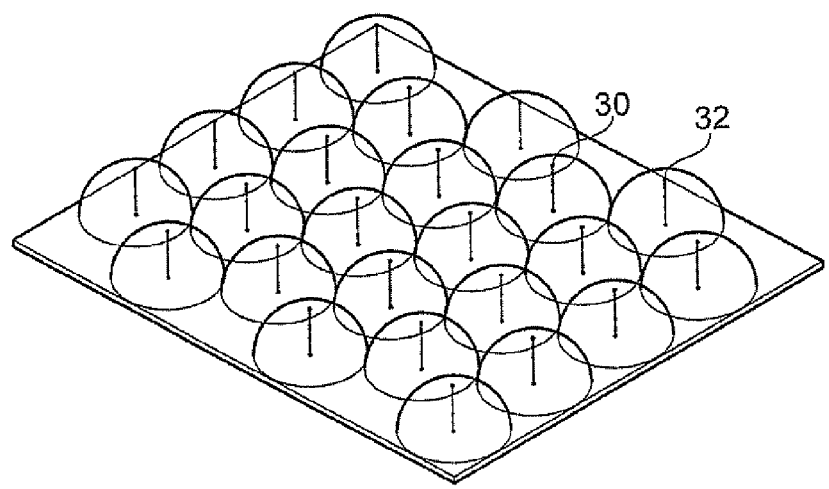
FIGS. 4A and B are diagrams showing an array of tethered biomolecules for use in a method of the invention at different inter-tether spacings.
Figure 4B:
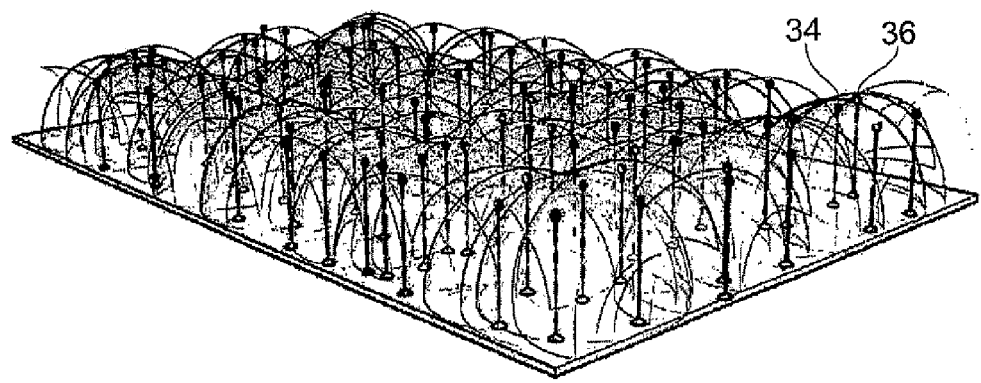
Figure 5:
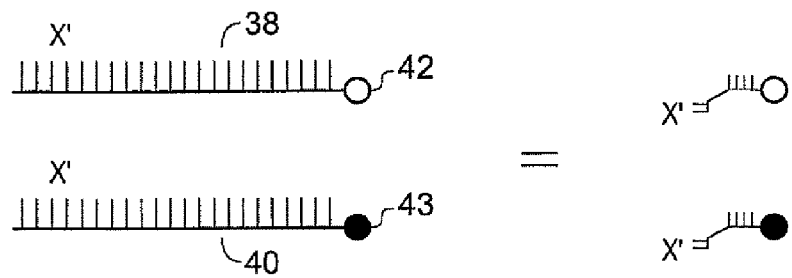
FIG. 5 shows head tether portions for use in tethers in accordance with the invention.

FIG. 3A shows the first and second biomolecules 10 and 20 binding in the reaction zone 28. As shown in FIG. 3B the tethers are flexible and so the biomolecules occupy a volume rather than just a surface. FIG. 4 shows varying the inter-tether spacing between tethered biomolecules. In FIG. 4A, the biomolecules, for example 30 and 32, are relatively spaced apart. In FIG. 4B, the biomolecules, for example 34 and 36, are relatively close together. An alternative to the random distribution of first and second biomolecules tethers as illustrated in FIGS. 4A and B is the targeting of first and second biomolecules to discrete portions on the surface of the substrate such that the first and second biomolecules can only interact if they stretch to span the gap between the surface patches. By controlling the distance between the discrete portions and/or the tether length, the proportion of bound and free biomolecules may be altered allowing the determination of affinity as described herein.

2 PREPARATION OF TETHERED ARRAY OF BIOMOLECULES

The preparation of one form of tethered biomolecules for use in a method in accordance with the invention is shown in FIGS. 5 to 9. This involves joining a variable length body tether to three "adaptor" oligonucleotides. The head, body, tail and anchor oligonucleotides are combined as described below to generate an immobilised tether. Arrays of spots containing immobilised tethers are produced with different proportions of first and second tether length tethers. As described later, nucleic acid-protein covalent complexes are then hybridised to the immobilised tethers.

a) Production of Tether Head Port Ions

Figure 6:
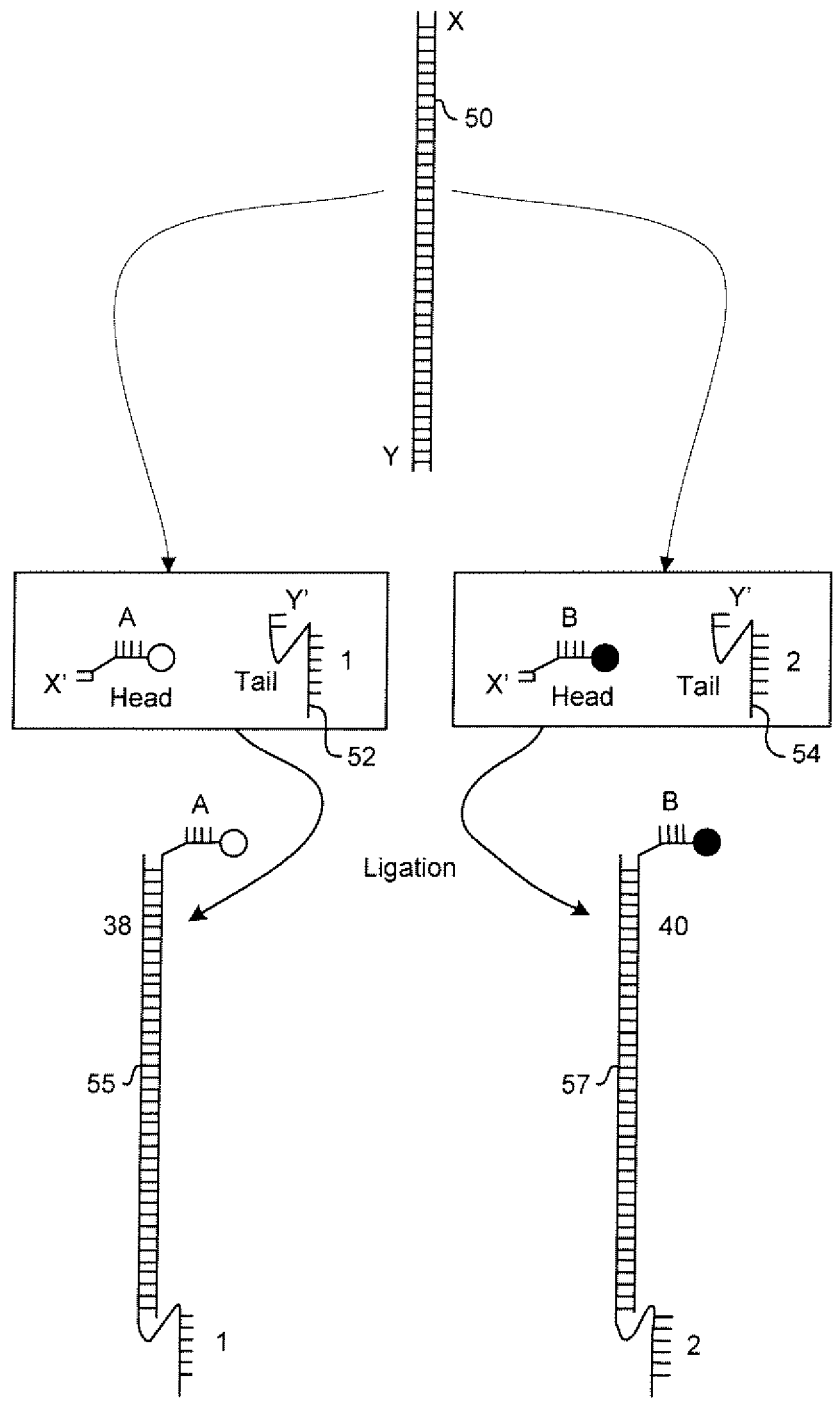
FIG. 6 shows a modified oligonucleotide for use in tethers in accordance with the invention.

Tether body portions are generated from double stranded DNA (dsDNA) as shown particularly in FIG. 6. A tether body portion 50 has a single-stranded upper portion comprising a restriction enzyme half site X, which is complimentary to the half-site X' of tether head portion 38 or 40. The lower region of the body tether portion includes a single stranded section, generally designated as Y in FIG. 6.

b) Production of Tether Body Portions

Tether body portions are generated from double stranded DNA (dsDNA) as shown particularly in FIG. 6. A tether body portion 50 has a single-stranded upper portion comprising a restriction enzyme half site X, which is complimentary to the half-site X' of tether head portion 38 or 40. The lower region of the body tether portion includes a single stranded section, generally designated as Y in FIG. 6.

c) Production of Tether Tail Portions

Tether tail portions are designed to anneal and ligate to the dsDNA tether body portion and also to anneal to specific anchor oligonucleotides which are described below. The tether tail portions 52 and 54 shown in FIG. 6 each comprise upper respective and lower sections. The upper section, generally designated as Y', is complimentary to the single stranded portion Y of tether body portion 50. The lower sections, generally designated as 1 and 2, are also single-stranded and are designed to anneal to the anchors described below.

d) Assembly of the Tethers

Separate tether production reactions are set up to generate pools of first or second fluorophore or to quantum dot labelled tethers with different tether lengths. The tether head portions 38, 40, tether body portions 50 and tether tail portions 52, 54 are assembled by conventional conditions under suitable conditions in solution as shown in FIG. 6 to form tethers 55 and 57. Typical conditions may be 50 mM NaCl, HEPES buffer pH7.5 (10 mM), and room temperature.

e) Anchor-Oligonucleotides

Figure 7:
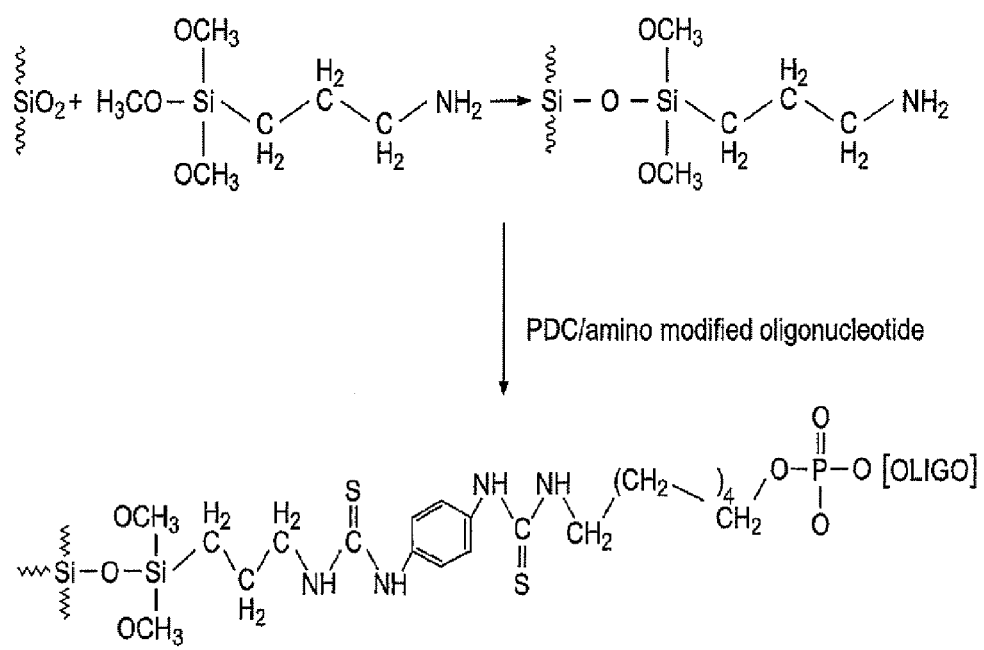
FIG. 7 shows the formation of tethers in accordance with the invention.

The assembled tethers 55, 57 can be anchored to a surface by means of anchors. The anchors are typically single-stranded amino-modified oligonucleotides. In a preferred embodiment, the solid support is a modified glass substrate prepared using standard techniques to covalently couple the anchor oligonucleotide. For example, see: Chrisey, L. A., Lee, G. U., and O'Ferrall, E. (1996) Covalent attachment of synthetic DNA to self-assembled monolayer films *Nucleic Acids Res.* 24:3031-3039. The amino-modified anchor oligonucleotides are coupled to glass treated with amino silane and p-phenylene1,4 diisothiocyanate (PDC) (FIG. 7).

In the specific implementation described below (FIGS. 13-15), Forster Resonance Energy Transfer (FRET) coupled with Fluorescence Life-time Measurement (FLIM) was used to determine the proportion of A and B that were molecularly close in an AB complex. FLIM exploits the time-dependence of FRET to allow more sensitive measurements of the proportions of A and B that are found in AB complexes. Both FRET and FLIM were used in the assays shown.

Figure 8:
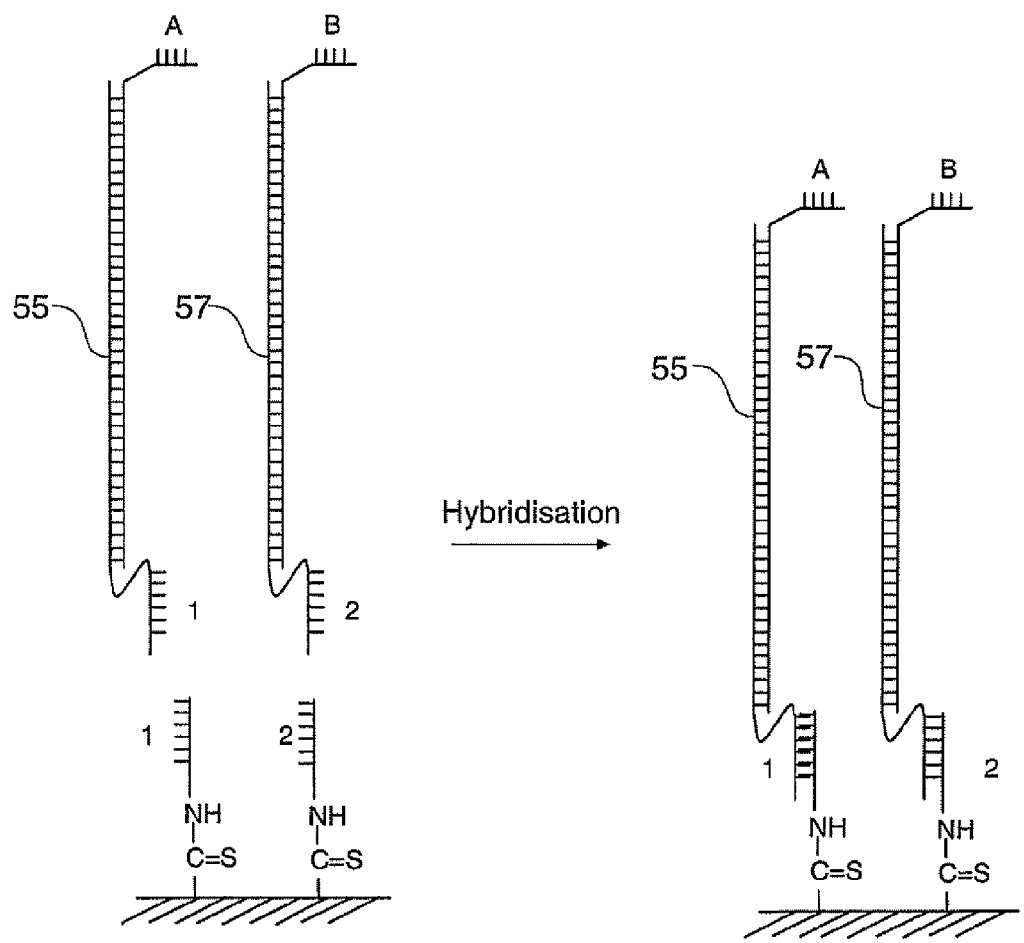
FIG. 8 shows a further step in the formation of tethers in accordance with the invention.

As shown in FIG. 8, the tethers 55 and 57 are then hybridised to a solid support 60 to which anchor oligonucleotides 56, 58, each having single-stranded sections, generally designated as 1 and 2 respectively, which are complimentary to corresponding sections 1 and 2 of the tether tail portions 52, 54, have been previously immobilised.

3 PRODUCTION OF TETHER/BIOMOLECULE CONJUGATES a) Use of In Vitro Translation

Protein biomolecule/nucleic acid conjugates which can hybidise to the tethers are produced according to the method described in: Jung, G. Y., and Stephanopoulos, G. (2004). supra by an in vitro translation reaction to covalently attach a nascent peptide by its C-terminus close to the 3' end of an mRNA-DNA conjugate. Tether protein complexes are then hybridised to the annealed arrays of tethers attached to their immobilised anchor oligonucleotides.

Figure 9:
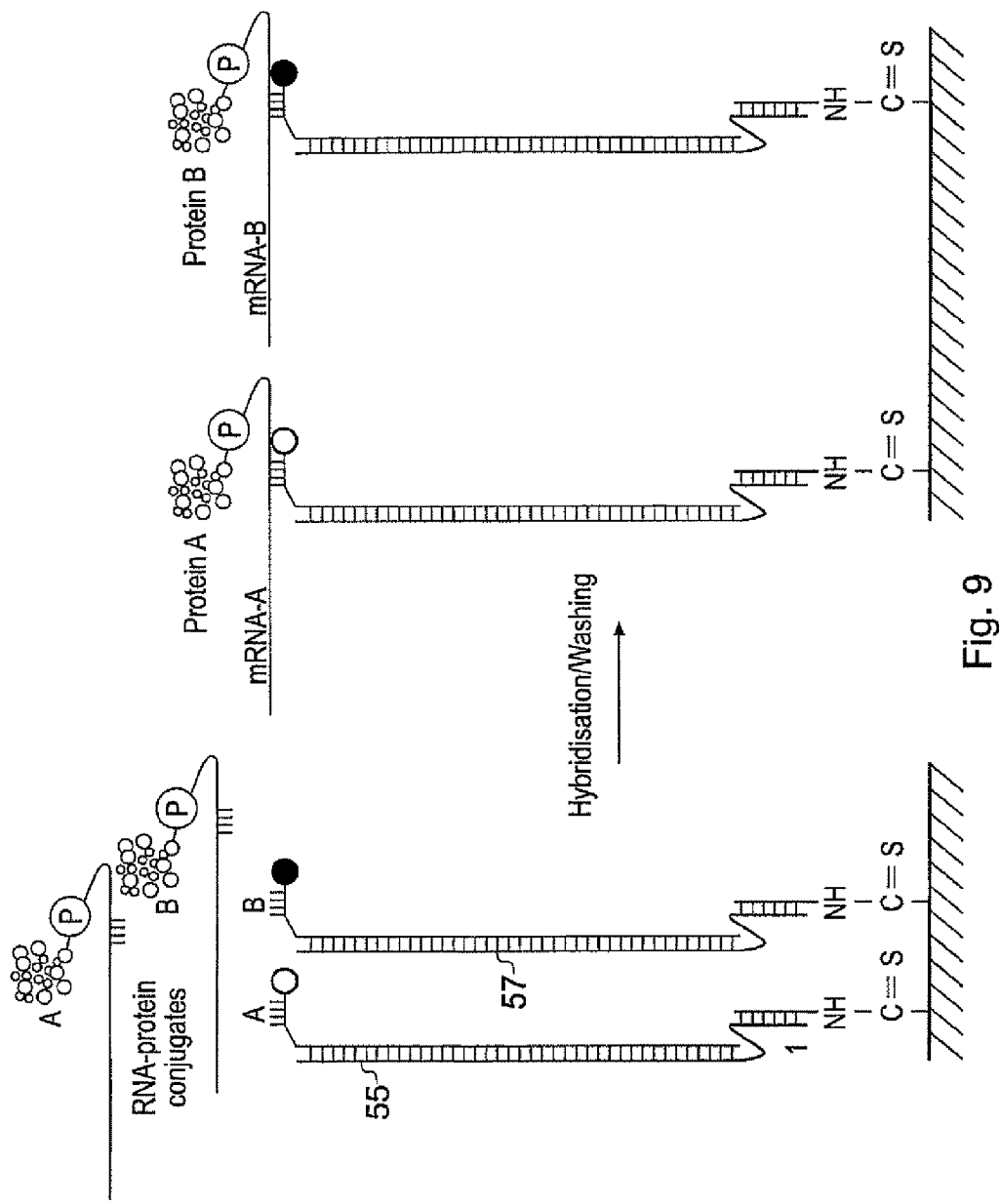
FIG. 9 shows the production of biomolecule and tether conjugates.

This is schematically illustrated in FIG. 9 where a first biomolecule, indicated generally as Protein A, is hybridized to the head portion of tether 55 and a second biomolecule, indicated generally as Protein B is hybridized to the head portion of tether 57. Alternative methods of making protein biomolecule-nucleic acid conjugates may be used, including the direct chemical crosslinking of purified first or second biomolecules to modified oligonucleotides.

b) Generation of Protein-Nucleic Acid Complexes In Situ

Alternatively, protein nucleic acid complexes may be generated in situ by annealing the mRNA-DNA conjugate to the immobilized tether first and translating the messenger RNA whilst bound to the tether by adding in vitro translation extracts to the tethered messenger RNA.

c) Use of Protein-Protein Fusions

In another approach, the messenger RNA is engineered to generate protein fusions between the protein biomolecule of interest and a second protein domain X. The domain X is designed to have a very high affinity for an engineered component of a tether head portion oligonucleotide or the head end of the tether. For example, where the X domain is a high affinity specific DNA binding protein (e.g. lambda repressor), its cognate DNA site is introduced into the head oligonucleotide complex to enable the nascent protein to associate with the tether via the DNA binding moiety. Alternatively, X is a molecule such as streptavidin and its binding partner—in this case biotin—is chemically coupled during synthesis to a tether head portion oligonucleotide.

4 ANNEALING OF NUCLEIC ACID-PROTEIN CONJUGATES TO TETHERS

In the preferred method, nucleic acid biomolecule protein conjugates are annealed through complimentary sequences (A or B) close to the 3' end of the nucleic acid component to complementary sequences in the head tether portion as shown in FIG. 9. This concentrates the nucleic acid conjugates from molarities typical of in vitro translations (e.g. 10 nM) to the experimental concentrations (e.g. 3.7 µM based on a 200 bp tether without any tether overlap; see Table 2) which shows the relationship between DNA length and other parameters for a individually-spaced tethered molecules.

TABLE 2

| Bases | Length | Volume | Molarity |
|---|---|---|---|
| 200 | 60 nm | 0.4 aL | 3.7 µM |
| 2 Kb | 600 nm | 0.4 fL | 3.7 nM |
| 20 Kb | 6 um | 0.4 pL | 3.7 pM |

As noted above the tethers need not be made from dsDNA but may be made from other molecules such as DNA DX hybrids.

5 MEASUREMENT OF AFFINITY IN SOLUTION

The measurement of affinity between first and second biomolecules A and B can also be carried out in solution, allowing the basic principle underlying the tethering principle to be investigated using the simplified scheme shown in FIG. 12A. In this method, A and B are attached at opposite ends of a single flexible tether allowing both molecules to sweep out a shared spherical volume that varies as a cubic function of the tether length. As the length of the single tether is reduced, the volume swept by A and B reduces and the effective concentration of A and B within the volume rises as a cubic function of the tether length. This scheme is formally analogous to the surface anchoring of tether biomolecules described above in that A and B can be regarded as being anchored to a surface that is exactly half the length of the joint tether such that the volumes swept by A and B exactly overlap.

In the specific examples described below, Forster Resonance Energy Transfer (FRET) coupled with Fluorescence Life-time Measurement (FLIM) was used to determine the proportion of A and B that were molecularly close in an AB complex. FLIM exploits the time-dependence of FRET to allow more sensitive measurements of the proportions of A and B that are found in AB complexes. Both FRET and FLIM were used in the assays shown. (Backsai et al (2003) J Biomed Opt. 2003 July; 8(3):368-75; Förster T (1965) Delocalized excitation and excitation transfer. In Modern Quantum Chemistry, part III. O. Sinanoslu, editor. Academic Press, New York. 93-137. Stryer L and Haugland R P, (1967) Proceedings of the National Academy of Science USA. 58: 719-730.).

EXAMPLE 1 a) Oligonucleotide Labelling and Preparation of 'Head Sets'

The details of the test system are illustrated in FIG. 13. The biomolecules whose affinity was measured were complementary strands of a DNA hybrid in which two 11 base pair overlaps recognise each other in a reversible reaction. The 11 base pair interacting regions are single-stranded DNA extensions of longer double stranded DNA molecules that contain fluorophores A (Acceptor) and D (Donor) incorporated into the bases indicated in bold (FIG. 13A). In the data shown, the fluorophore used as donor was Alexa Fluor 488 and at the fluorophore used as acceptor was Alexa Fluor 555, both are manufactured by Molecular Probes. Both fluorophores were incorporated during oligonucleotide synthesis and the labelled oligonucleotides were subsequently annealed to form the structures shown in FIG. 6A. The fluorophore-tagged double-stranded oligonucleotides are referred to as a donor or acceptor 'head set' to denote the presence of both the annealing 11 bp affinity region and the presence of the fluorescent dyes.

b) Linear DNA Tether Preparation

To make the longer tethered molecules illustrated in FIG. 13B and schematically in FIGS. 12A and 12B, the donor and acceptor head set oligonucleotides were ligated to variable length double stranded DNA regions by standard procedures. Briefly, the 'head set' oligonucleotides were cleaved with Bst X1 restriction enzyme and were ligated to variable length 'tether body' DNAs each of which contained a free BstX1 and Xba1 site. BstX1-BstX1 and Xba-Xba ligations were used to generate the molecules as shown in FIG. 5B. These were gel purified prior to analysis. The total lengths of the linear molecules incorporating both Donor and Acceptor head groups were: 515 bp and 710 bp.

c) Sample Preparation, FRET and FLIM Detection

Head sets or dual-labelled linear DNA molecules were diluted to the concentrations described in a final concentration of 70 mM NaCl, 10 mM Tris pH 8.0. 6 µl of each solution was introduced into one of the wells of a 50 well slide produced using a multi-chambered coverslip (Stratech Scientific, UK) together with a 22×50 mm coverslip (Menzel-Glaser, Germany).

Samples were analysed using a frequency-doubled Ti:Sa laser providing short optical pulses (100 fs duration) at 76 Mhz repetition rate, with wavelength in the absorption band of the donor fluorophore (~470 nm). The exciting light was weakly focused onto the sample allowing for a uniform illumination and collection over 1 mm well depth, to maximize the signal contribution over the fluorescence background of the coverslip. Low excitation intensities (0.05-10 mW over 0.4 mm spot diameter) were maintained to avoid nonlinearities and photodamage. Fluorescence light collected from a microscope objective was spectrally analysed using a spectrometer and detected by a cooled CCD camera for time-integrated FRET spectra. For time-resolved FLIM, fluorescence light was filtered by the spectrometer around the emission maximum of the donor fluorophore (520±5 nm) and detected by a single channel fast photomultiplier (200 ps time resolution) connected to a time-correlated single photon counting module. Background contributions were measured from the buffer solution without fluorophores in the same excitation and detection conditions and properly subtracted to the data.

d) Preparation of a Y-Shaped Module

The first and second tether portions for each biomolecule in a Y-shaped molecule are anchored to a single DNA strand such that the tethers are free to diffuse as for the linear molecule shown in FIG. 12B. The main advantage of this form of tethering compared with that of the single molecule is that the first and second tether portions are free to interact independent of the length of the intervening tether. By contrast, the linear molecule is unable to fold back on itself at lengths shorter than the persistence length (P) which approximates to between 90 and 120 bp.

e) Data Analysis

To determine the % maximal binding, we first determined the proportion of bound and unbound donor (R) at different donor and acceptor concentrations using the following procedure. The ratio between the bound and unbound decay spectra for different acceptor concentrations was determined over time and plotted as shown in FIG. 14 using free labelled head set oligonucleotides (The three curves shown represent 1. 50 nM acceptor:50 nM donor, 2. 200 nM acceptor:50 nM donor, 3. 600 nM:50 nM donor).

For each curve a numerical fit (dotted lines) to the decay curve $(R(t)=U(1+R \exp(-t/\tau)))$ was performed, where R=ratio between bound and unbound donor, t=time, U=N(unbound)/N (where N=concentration of donor in the absence of acceptor). $\tau$=decay constant. R, U and $\tau$ were directly determined from the numerical fit of the experimental data.

The proportion of bound donor=R/(1+R) was plotted against acceptor concentration as shown in FIG. 15 (percentage normalised to the maximum effect observed above 4000 nM acceptor concentration). In FIG. 15, the experimental curve of free donor and acceptor head sets was determined for a range of acceptor head set and a single (50 nM) donor head set concentration. This allowed the determination of the binding affinity of the 11 bp overlap head sets as 136 nM. This matches closely to the theoretical determination of 176 nM for the same sequence. In FIG. 16, preliminary data from two 11 bp overlap linear molecules (donor at one end, acceptor at the other; open circles) is displayed on the same scale.

f) Theoretical Determination of DNA Binding Affinity

Assuming a chemical reaction between molecules A and D in order to form bound molecule AD:

$$A+D \leftrightarrow AD \quad (1)$$

as well as a reverse reaction and that the system is in equilibrium, we can define dissociation constant:

$$k_d=[A][D]/[AD] \quad (2)$$

Note that according to the basic textbooks (see for example John SantaLucia, Jr. and Donald Hicks. (2004) Annu. Rev. Biophys. Biomol. Struct. 33, 415-40), people also use equilibrium constant $k_{eq}=1/k_d$.

$$k_d=1/k_{eq}=\exp(\Delta G/RT) \quad (3)$$

where $k_d$ [mol/l] is dissociation constant, $\Delta G$ [cal/mol] is change of the free energy due to reaction, R=1.987 [cal/(K mol)], T [K] absolute temperature. In order to calculate $k_d$ we have to calculate $\Delta G$. In our case we have DNA headsets with different base pairs overlap.

This can be done by methods and software developed by Prof. SantaLucia and co-workers John SantaLucia, Jr. and Donald Hicks. (2004) supra, Annu. Rev. Biophys. Biomol. Struct. 33, 415-40.

In order to estimate properly $\Delta G$ for DNA molecules we have to take in account folding and hybridization prediction (M. Zuker. Nucleic Acids Res. 31 (13), 3406-15, (2003)).

The final results are presented in the following tables. The theoretical affinities were calculated using methods described in the following references: John SantaLucia, Jr. and Donald Hicks. (2004) supra; M. Zuker, (2003) supra; and A V Fotin et al, Nucleic Acids Res. 26 (1998) p. 1515.

TABLE 3

Prediction of $\Delta G$ for DNA headsets for salt concentration 70 mM.
SALT CONCENTRATION 70 mM, TEMPERATURE = 21° C. (274.15K)

| BASE PAIRS | dG[kcal/mol]/K [M] (thermodynamic prediction) | dG[kcal/mol]/K [M] SantaLucia Correction due to folding (thermodynamic prediction) | dG[kcal/mol]/K [M] SantaLucia correction due to folding (net hybridization thermodynamics) | dG[kcal/mol]/K [M] Fotin correction due to folding (thermodynamic prediction) | dG[kcal/mol]/K [M] Fotin correction due to folding (net hybridization thermodynamics) |
|---|---|---|---|---|---|
| 11 | −13.5/1.06304E−10 | −9.14/1.7685E−7 | −6.01/3.63052E−5 | −10.3/2.45826E−8 | −7-17/5.0465E−6 |
| 9 | −9.19/5.85332E−8 | −5.99/3.75616E−5 | −5.84/4.84797E−5 | −6.59/1.35357E−5 | −6.44/1.74701E−5 |
| 7 | −6.93/7.59095E−6 | | | | |
| 5 | −4.34/6.219E−4 | | | | |

TABLE 4

Prediction of ΔG for DNA headsets for salt concentration 35 mM.
SALT CONCENTRATION 35 mM, TEMPERATURES = 21° C. (274.15K)

| BASE PAIRS | dG[kcal/mol]/K [M] | dG[kcal/mol]/K [M] SantaLucia Correction due to folding | dG[kcal/mol]/K [M] SantaLucia correction due to folding (net hybridization thermodynamics) | dG[kcal/mol]/K [M] Fotin correction due to folding | dG[kcal/mol]/K [M] Fotin correction due to folding |
|---|---|---|---|---|---|
| 11 | −12.75/3.80743E−10 | −8.5/5.25316E−7 | −5.72/5.94583E−5 | −−9.54/8.95563E−8 | −6.77/9.966E−6 |
| 9 | −9.19/1.6243E−7 | −5.48/8.94373E−5 | −5.36/1.09691E−4 | −5.99/3.75616E−5!!! | 5.87/4.607E−5!!! |
| 7 | −6.48/1.63209E−5 | | | | |
| 5 | −4.04/0.00104 | | | | |

The results presented in Tables 3 and Table 4 for 11 base pairs with a correction due to the folding depend on the methods for the calculation which is used either SantaLucia or Fotin. The difference is one order of magnitude. For 9 base pairs the agreement between two methods is better.

Results a) Determination of the Binding Affinity of the 11 bp Overlap Using Free Oligonucleotides An essential initial goal of these studies was to determine an accurate value for the 11 bp affinity to enable later comparison with results using the nano-tether methodology of the invention. Standard titration reactions were carried out to identify the dissociation constant ($K_d$) for the oligonucleotides shown in FIG. 13A. Essentially, this involved creating multiple samples with a fixed concentration of fluorescently-labelled donor head-set oligonucleotides (D; 50 nM) with a variable concentration of fluorescently-labelled acceptor head set oligonucleotides (A; 0 nM-5000 nM).

To determine the amount of D:A hybrids, the samples were analysed for the time-dependence of FRET-FLIM as described above. A representative plot from this analysis is shown in FIG. 14. The rate of decay of the fluorescence signal is increased in the presence of increasing levels of fluorescently-labelled acceptor head sets showing increased decay rate of the donor fluorophore in the presence of the acceptor fluorophore that is a time-dependent characteristic of FRET. Importantly, labelled head sets that did not contain a single-stranded overhang showed no FRET/FLIM (data not shown), arguing that the decay observed was due to the inter-molecular hybridisation of the two head-sets.

The characteristic decay curves from FRET-FLIM analyses of the kind shown in FIG. 14 were transformed into relative FLIM values according to the method described above and were plotted in relation to the concentration of Acceptor Head-Set oligonucleotide (FIG. 15). Specifically in this figure the percentage maximum FLIM (y-axis) for the 11 bp overlap donor head set was plotted against the acceptor head-set concentration. The curve showed a classical saturation response with a half maximal binding ($K_d$) concentration of Acceptor head set being calculated (FIT) to be 136 nM. Linear regression analysis was used to estimate a value of 136 nM for the dissociation constant of the 11 bp overlap in 70 mM NaCl. This value was very close to the theoretical value of 170 nM that was calculated for the sequence from nearest-neighbour thermodynamic predictions (see above). This indicates that the FRET-FLIM method was able to accurately determine the proportion of bound fluorophores.

b) Tether Length-Dependence of FLIM on Linear Molecules

The proportion of linear tether molecules found in the bound form increased as the length of the tether decreased according to predictions (FIG. 12A,B). To test this, linear molecules with an 11 bp overlap donor head set at one end and an acceptor head set at the other were generated as described above. The data obtained is represented in the table below. Preliminary data on FRET/FLIM for the linear molecules is indicated in open circles in FIG. 16 and Table 5. (A more complete data set on a greater number of DNA lengths is shown in FIG. 22). The preliminary data points are for a 515 bp and a 710 bp linear DNA; each with an 11 bp overlap. The ends of each molecule were labelled at one end with Alexa Fluor 488 and at the other with Alexa Fluor 555. The actual concentration of each molecule was 5 nM and the nominal tethered concentration of each molecule was 778 nM and 2000 nM as determined by assuming each molecule has a volume whose spherical radius is the length of the tether. As can be seen from the graph, the measured FRET values were much higher than expected based on the absolute molecular concentration (5 nM) and were higher for the shorter molecule (515 bp) than for the longer molecule (710 bp). This data is consistent with the tether enhancing the concentration of the free ends in proportion to the inverse of the length of the tether. In addition, the data is consistent with the claims that concentration can be altered by varying the length of the tethers.

TABLE 5

| Length p [bp] | f = [AD]/D | U | R | τ [ns] | $[A]_{TOT}$ [nM] | $[D]_{TOT}$ [nM] | [A] [nM] |
|---|---|---|---|---|---|---|---|
| 710 | 0.1181 | 0.8905 | 0.134 | 0.5569 | 778.15 | 778.15 | 686.25 |
| 515 | 0.2922 | 0.7299 | 0.413 | 0.6724 | 2039.0 | 2039.0 | 1443.2 |

The percentage maximal FLIM was plotted against nominal tethered concentration in FIG. 16 showing that FRET/FLIM and therefore binding increased at shorter tether lengths. In FIG. 16, the percentage maximum FLIM for the 11 bp overlap donor head set was (as in FIG. 15) is shown a gain for reference, plotted against the acceptor head-set concentration. The data shows that the measured percentage FLIM for each length of tether was comparable to that generated by using free concentrations of the same ligand as shown in FIG.

15, suggesting that the tethers maintain their ends within a volume similar to that generated by a flexible linear molecule.

EXAMPLE 2

Experimental Details

The generation of the data shown involved the preparation of fluorophore-labelled linear DNA molecules and the measurement of time resolved FRET.

1. Preparation of Reagents a) Design of the Head Sets

Figure 19C:
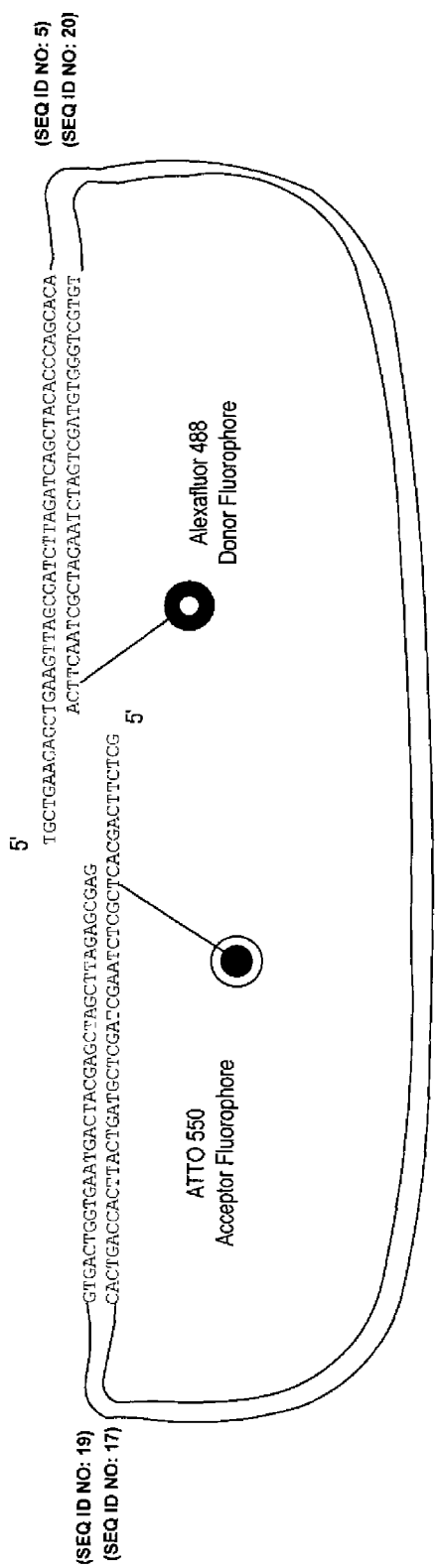
Figure 19D:
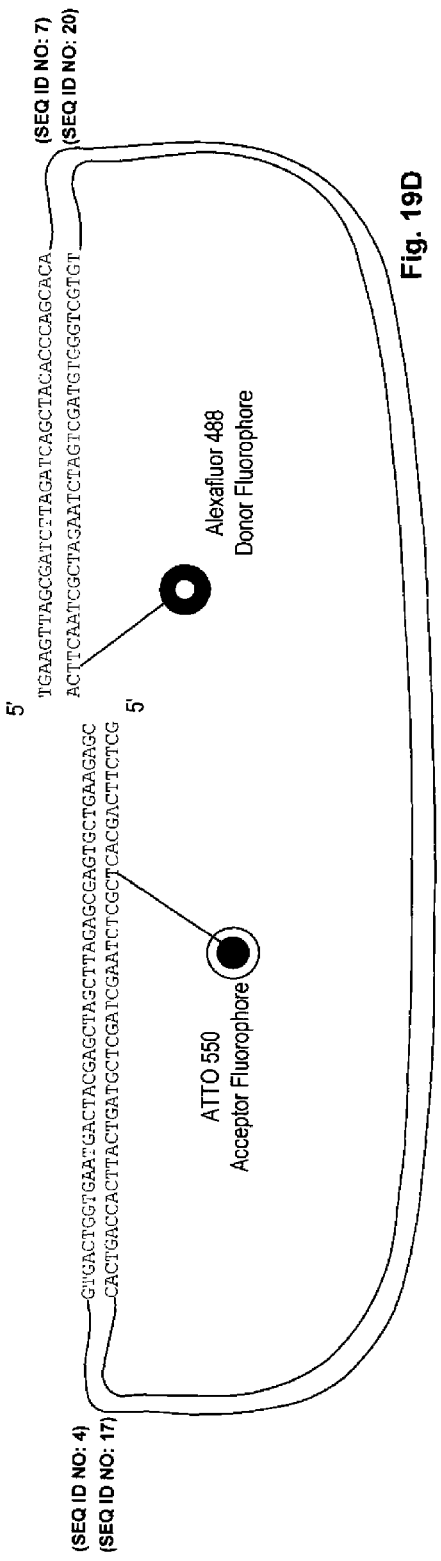

The biomolecules whose affinity was measured are shown in FIG. 19. The key points are an 11 bp overlap between two pairs of oligonucleotides that constitutes the biological affinity to be measured, together with covalently-coupled fluorophores that are required for the measurement of free and bound molecules using time-resolved FRET. These molecules are essentially the same as described in Example 1 above (FIG. 13A) which contain the same 11 bp overlap single-stranded DNA overlap. The main difference between those sequences and the sequences of this example is the presence of a BstX1 half site to allow ligation onto the Tether Body DNAs (FIG. 19C,D).

The overlapping oligonucleotide pairs are called 'Head Sets' and they are distinguished by the attached fluorophore. The donor fluorophore (Alexafluor 488) and Acceptor (ATTO550) fluorophores were attached to the oligonucleotides during synthesis by commercial suppliers (Eurogentec) and are attached to bases indicated.

As a control, analogous fluorophore-labelled Head Set blunt-ended oligonucleotides were synthesised that have no single stranded overlap (0 bp overlap; FIG. 19B).

b) Annealing and Ligation to the Tether Body

The 2 constituent oligonucleotides for the donor or acceptor Head Sets (25 µM final concentration) were annealed by cooling from 90° C. to room temperature over 1 hour in a thermal cycler machine in annealing buffer (70 mM NaCl 10 mM Tris pH 7.4).

Following annealing, 1.5 µl of a 25 µM solution of each of the donor and acceptor Heat Sets (~5 fold molar excess) was ligated to various length 'Tether Body' DNAs to generate linear molecules with a terminal donor and acceptor Head Set according to standard procedures ((Sambrook et al., 1989); FIG. 19C,D). An gel analysis example of the ligation reactants and products is shown in FIG. 20 (1% Agarose Gel stained with ethidium bromide according to standard procedures (Sambrook et al., 1989). This shows that the linear Tether Bodies increased in size following the ligation of the donor and acceptor Head Sets.

The DNAs that were analysed by FRET (FIG. 20) were 498 bp, 692 bp, 1052 bp and 1752 bp in length following addition of the Head Sets. To ensure that each Tether Body attached to 1 donor and 1 acceptor Head Set, the ligation overlap sequences were designed to be different in sequence and non-palindromic (Acceptor Headset 5'TCAC; Donor Headset 5'CACA). This was achieved by BstX1 digestion of the Tether Body DNAs from plasmids that contained two BstX1 sites flanking the region Tether Body region of DNA.

Following ligation, the linear molecules were gel purified and quantified by comparison with known DNA standards. For FRET analysis, the samples were diluted to the concentrations indicated and 5 µl was added to the wells of a multi-well chambered coverslip (Grace Bio-labs; CWCS 50R-1.0). The wells were sealed with a standard glass coverslip.

2. Time-Resolved FRET Analysis a) Data Acquisition

Samples were analysed using a frequency-doubled Ti:Sa laser providing short optical pulses (100 fs duration) at 76 Mhz repetition rate, with wavelength in the absorption band of the donor fluorophore (~470 nm). The exciting light was weakly focused onto the sample allowing for a uniform illumination and collection over 1 mm well depth, to maximize the signal contribution over the fluorescence background of the coverslip. Low excitation intensities (0.05-10 mW over 0.4 mm spot diameter) were maintained to avoid nonlinearities and photodamage. Fluorescent light collected from a microscope objective was spectrally analysed using a spectrometer and detected by a cooled CCD camera for time-integrated FRET spectra. For time-resolved FRET, fluorescence light was filtered by the spectrometer around the emission maximum of the donor fluorophore (520±5 nm) and detected by a single channel fast photomultiplier (200 ps time resolution) connected to a time-correlated single photon counting module. Background contributions were measured from the buffer solution without fluorophores in the same excitation and detection conditions and properly subtracted to the data.

b) Data Analysis

The time dependence of FRET can be seen in the Donor and Acceptor dynamics shown in FIG. 21. The maximal fluorescence intensity of each trace was normalised to 1. As expected, the proximity of the Donor Fluorophore to the Acceptor Fluorophore (due to the binding of the 11 bp overlap sequences) resulted in a rapid decay of Donor fluorescence by comparison with unligated Donor Head Set oligonucleotides (FIG. 21A solid curves). A corresponding enhancement of Acceptor fluorophore dynamics was observed by comparison with the unligated Acceptor Head Set. Importantly, no energy transfer was observed in analogous experiments involving the 0 bp overlap linear molecules (FIG. 21B), indicating that the 11 bp overlap was required for the changes in fluorescence dynamics.

The proportion of bound (circular conformation) to total number of molecules [Dbound/Dtot] is proportional to the probability that the molecules are in the circular conformation and was calculated as described above.

The variation of the proportion of bound molecules with the length of DNA is shown in FIG. 22. The proportion of bound molecules closely matched the theoretical values predicted from models of DNA end concentration ($J_M$ factor) as calculated from according to Rippe et al., (Rippe, 2001) (see x symbols). It is important to note that the theoretical curve shows a maximum local end concentration ($J_M$ factor) close to the persistence length of the DNA. A similar peak is observed in the experimental data. The practical basis for the maximum is that below a certain length, (the persistence length), the DNA ends cannot fold back to bind each other due to the stiffness of the DNA. By contrast, once the DNA has exceeded a length required to fold back on itself a maximum level of binding is observed. Further increases in length result in a lower probability that the free ends will encounter each other. These characteristic changes in binding are the property that the methods of the invention will use to determine the binding affinity of unknown binding partners.

The second major point to note is that the proportion of bound molecules was not markedly affected by a 10 fold dilution (10 nM to 1 nM; FIG. 22). This contrasts with the strong concentration dependence of the free molecules as shown in FIG. 15. This fact is consistent with our contention that nanotether affinity measurements should be highly sensitive. Theoretically, the sensitivity of measurements using methods in accordance with the invention should only require multiple measurements of a single pair of molecules. However, in some implementations of the method, many molecule pairs will be probed simultaneously (>100,000) to maximise the signal output.

Discussion

The results show that tethered biomolecules at each end of a linear DNA tether occupy an effective volume that is close to that predicted on the basis of the swept volume of their contour length, d $(4/3.pi.(d/2)^3)$. The data shows that varying the length of the tether alters the effective concentration of the ends.

These results show that tether length can be used as a direct way of controlling the concentration of biomolecules at the free ends of the tethers and that a high 'concentration' of tethered biomolecules can be obtained via an intra-molecular interaction between a pair of biomolecules at the end of the tether.

The results show that FRET/FLIM analysis is a practical way of assessing the proportion of bound biomolecules attached at the end of the tethers. As the percentage of interacting molecules is dependent on the length of the tether and not on the concentration of the tethers, it is, in principle, possible to measure the affinity of a pair of tethered molecules by taking multiple FRET/FLIM readings on a single tethered molecule. However, with the sensitivity of existing fluorescence technologies, we estimate that FRET/FLIM analyses will require at least 10,000 tethered molecule pairs necessary to estimate an equilibrium binding constant since readings will need to be made with as few as 10% of bound pairs 1,000 molecules. Nonetheless, this number of molecules is in the attomole range and argues that the technique should be as sensitive as discussed above.

Although the preferred method for tethering the biomolecules is to attach them to a solid surface, the connection of two biomolecules via a single flexible tether is essentially a minor practical modification of the linear tether system described since the primary control over tethered biomolecule concentration will be attained by altering the tether length. However, the surface tethered method should also allow fine control of the overlap between swept volumes by altering the inter-anchor distances (see FIGS. 1 to 4).

Nonetheless, we note that the linear molecule and other implementations of the nano-tether biochemistry approach such as the Y-shaped molecule (FIG. 17) may have distinct advantages in settings in which the detection molecules are introduced into containers containing factors that may alter the affinity of the two biomolecules. For example, vesicle preparations containing the linear or Y-shaped molecules could be used to monitor the concentration of a metabolite that alters the affinity of a first biomolecule for a second biomolecule and is free to diffuse into the vesicle. Potential containers include test tubes, microwell plates, membrane-bound containers that allow diffusion of metabolites, but retain the linear molecule, cells (e.g. microinjection of molecules), and organisms (e.g. Zebra fish embryos).

6 FORMAT FOR METHODS/APPARATUS OF THE INVENTION a) Glass Slide Format

In one embodiment, the format of the support is a glass slide onto which oligonucleotides have been printed in arrays of spots using a split pin arraying machine.

b) Microbead Format

In an alternative format, the support is provided by microbeads that are coupled in formats that generate a unique relationship between a single bead and tether combination. This format enables the adaptation of the technology to microfluidic systems.

c) Controlling the Inter-Anchor Spacing

Using the preferred arrayed-spot implementation, mentioned in section 6a) above, amino-terminal oligonucleotide anchors for the first and second biomolecules are covalently coupled to the modified glass substrate. A non-specific amino-terminal oligonucleotide (designed not to bind tether components) is titrated into the anchor oligonucleotide coupling mix to vary the inter-anchor coupling distance where appropriate. Inter-anchor mean distances are varied from lengths greater than the tether length to the maximal oligonucleotide tether capacity (maximal capacity is 20 pmoles of bound DNA/cm² which equates to an mean inter-anchor spacing of 1.6 nm; Chrisey, L. A., et al (1996)). This inter-anchor density massively exceeds that required for the typical range of anchor densities (e.g. to bring 200 bp (60 nm) tethers within a mean 30 nm of each other requires a mean spacing of 30 nm).

The non-specific oligonucleotide functions to cap the reactive groups and will also make the surface electrostatically negative, thereby minimizing the association of the negatively-charged DNA tether with the surface. Alternatively, hydrophobic lipid groups may be coupled to the glass surface to discourage DNA-surface association due to the incompatibility of hydrophobic-hydrophilic associations.

In an alternative implementation, the sequences present in the anchor oligonucleotide (sequences 1 and 2; of anchors 56 and 58 in FIG. 8) are synthesized in series (i.e. 5' sequence 1-sequence 2-3' as a single oligonucleotide). This will effectively generate a common anchor for both tethers A and B and will ensure that the swept volumes entirely overlap. There may be advantages to this approach if very low numbers (as low as 1 pair of biomolecules) were to be studied as part of further developments of the technique.

7 ASSAY READOUT a) Slide Mounted Systems

In one embodiment of the invention, the assay readout is the intensity of Forster resonance energy transfer (FRET) between the different fluorophores 42, 43 coupled to the tether head portions 38 and 40 or elsewhere in the nucleic acid portion of the tether as shown in FIG. 10. A laser appropriate to the excitation maximum ($\lambda$1) for fluorophore is used to excite that fluorophore. Emission at the wavelength maximum ($\lambda$2) from the fluorophore 43 is recorded to assess the level of FRET (FIG. 10). Alternatively, fluorophore 43 may be selected to quench fluorescence from fluorophore 42 through FRET. In practice, for FRET to occur, an excited molecule of one fluorophore has to be molecularly close (<10 nm) to another fluorophore for energy to be transferred leading to emission at the characteristic wavelength of the other fluorophore. This will occur in methods of the invention when the first and second biomolecules are also molecularly close due to the formation of complexes between the first and second biomolecules. Thus, the proportion of first and second biomolecule present within a tethered biomolecule spot is quantified by the intensity of FRET. Appropriate controls (e.g. spots of the fluorophores 42 and 43 alone) are used to normalise signal levels.

FRET is measured using a confocal microscope on glass slides containing arrays of tethered biomolecules.

b) Use of Nanoscale Spheres or Quantum Dots

In an alternative solution, nanoscale solids, such as spheres or "quantum dots" (Doty, R. C. et al Cell Mol. Life Sci. 61 (15) 1843-9), are tethered in place of the single fluorophores. These conjugates may offer higher FRET efficiencies due to the increased number of fluorescent molecules. Alternatively, the nanoscale solids would allow fluorescence correlation spectroscopy to be performed using a high-resolution light confocal microscope. For tethers longer than 2 Kb (0.6 µm), the formation of first and second biomolecule complexes can be directly recorded due to the proportion of fluorescent dots pairs in proportion to those that show some separation.

8 DATA ANALYSIS

Simple well characterised equilibrium binding equations (Michaelis Menten) are used to derive molecular interaction parameters based on the concentrations of the first and second biomolecules and the proportion of those biomolecules which are bound.

9 APPLICATIONS

Additional applications of, methods of the present invention, the nano-tether biochemistry technique, in all formats (linear, Y-shaped and attached) include:

a) Determination of $K_d$

For example, in a typical experiment to accurately determine the $K_d$ of an interaction, a range of tether lengths and inter-anchor distances are set up as an array of spots using appropriate combinations of anchors and tethers for the first and second biomolecules. This generates a standard range of concentrations. These concentrations are plotted against the proportion of bound first and second biomolecule complex and the concentration of the first biomolecule (or the second biomolecule) required for half maximal binding is determined (This concentration is the $K_d$).

b) Library Screening

The method of invention allows the screening of interactions between a single molecule A and a library of molecules B1, B2, B3 . . . $B_n$. In this format, each spot is occupied by only A and B1 or A and B2 . . . A and $B_n$. In a preferred implementation for protein molecules, head tethers recognising unique (for example coding) regions from the 3' end of messages B1, B2, B3 . . . $B_n$ are generated and coupled to the core tethers as described earlier. $B_n$ can be a library of proteins potentially representing the transcriptome/proteome. Alternatively, $B_n$ can be libraries of peptides used to defining interaction sites or tethered libraries of chemical compounds ranging from small molecule compounds to libraries of synthetic polymers.

c) $K_{off}$ Measurement

As illustrated schematically in FIG. 11, by using an anchor/tether for a second biomolecule that can be cleaved together with initial saturating concentrations of the first and second biomolecules, it is possible to determine $K_{off}$. In this arrangement, the rate of decay of levels of the complex of the first and second biomolecules is monitored in real time following cleavage of the tether for the second biomolecule. This type of analysis is analogous to that used in surface plasmon resonance to determine the $K_{off}$.

This may be achieved in two ways. For situations involving slow $K_{off}$ rates, restriction enzyme digestion of the anchor/tether releases the second biomolecule and allows it to diffuse away from the first biomolecule. For faster $K_{off}$ rates, a modified oligonucleotide containing a photo-cleavable moiety is incorporated into the single stranded region of the anchor. The photocleavage is initiated using a different wavelength of light from that used in FRET analysis. By knowing $K_{off}$ and $K_d$, $K_{on}$ can be calculated based on the equation $K_d = K_{off}/K_{on}$ d) Screening for Modulators of Biological Systems

By establishing binding constants between the first and second biomolecules that are close to the $K_d$, it is possible to set up binding reactions at concentrations of the first and second biomolecules that are close to the $K_d$ and thus are particularly sensitive to screens for soluble modulators of their interaction. These modulating molecules will collectively be called "C". Examples of C include: a purified interacting protein, a protein that modifies A and B (e.g. a kinase), a drug molecule or candidate, complex mixtures of proteins that contain one or more components that alter AB complex formation (e.g. cell extracts, blood serum, other biological fluids). C could be a solution of a single molecule or complex mixtures of compounds (e.g. biological extracts or bodily fluids). C may itself be tethered to a third tether or alternatively it may be non-tethered, for example, in solution according to the application. The presence of C can be tested in a number of formats as described below with reference to FIG. 18.

Format 1. An array of different first and second tethered biomolecule pairs is treated with C to determine the range of binding reactions that C affects. The tether lengths of A and B can be adjusted such that their effective concentration would be close to the $K_d$ of the AB complex. At this concentration, 50% of AB would be present in the complex and the interaction would be most sensitive to factors that alter the strength of AB interaction. Factor 'C' may increase or decrease the affinity of A for B by interacting with or modifying either or both of A and B.

Format 2. The same tethered pair of first and second biomolecules is treated with different C compounds by tethering the first and second in separate reaction wells (e.g. microwell plates).

Format 3. Continuous Flow. The same tethered pair of first and second biomolecules arranged in a column format or an array of microbeads or in a microfluidic system will be treated in a flow of C. In this case, C may be a sequential series of test solutions or fractions from a separation (e.g. Chromatography column eluates in a combinatorial chemistry system, or protein fractions from a cellular extract).

Format 4. Measurement of concentration of known 'C.'s. When the affinity of a Factor 'C' for A, B or an AB complex is known, the concentration of Factor C can be measured. This could be used for example to determine the proportion of biomolecules in clinical samples such as serum.

The invention claimed is:

1. A method of measuring the affinity of a first and a second biomolecule, wherein the first biomolecule is tethered by a first tether portion having a first tether portion length and a first tether persistence length and the second biomolecule is tethered by a second tether portion having a second tether portion length and a second tether persistence length, wherein the first and second biomolecules are tethered to a surface, such that swept volumes defined by the movement of each biomolecule overlap, so that the first and second biomolecules are able to bind to each other, said method comprising determining a proportion of the first and second biomolecules bound to each other.

2. The method according to claim 1, wherein a range of the first and second tether portion lengths produce a range of effective concentrations for the first and/or second biomolecules.

3. The method according to claim 2, wherein said method further comprises determining the binding of the first and second biomolecules in the presence of a third biomolecule.

4. The method according to claim 2, wherein the length of the first and/or second tether portion are different.

5. The method according to claim 1, wherein the at least one tether portion comprises nucleotides.

6. The method according to claim 1, wherein the at least one tether portion comprises a double-stranded DNA.

7. The method according to claim 1, wherein the at least one tether portion comprises a carbon nanotube, an amyloid fibril, or a polymer.

8. The method according to claim 7, wherein the polymer is a DNA crossover complex.

9. The method according to claim 1, wherein said first and/or second tether portions are made from double-stranded DNA, DX hybrids, carbon nanotubes, amyloid fibrils, or polymers to produce a range of effective concentrations for the first and/or second biomolecules.

10. The method according to claim 1, wherein the proportion of the first and second biomolecules that are molecularly close to each other indicates the proportion of interacting the first and second biomolecules.

11. The method according to claim 1, wherein the proportion of binding of the first and second biomolecules is determined by the intensity of fluorescence (Förster) resonance energy transfer (FRET) between a first and second fluorophores respectively attached to, or integrated with, the first and second biomolecules.

12. The method according to claim 1, wherein the $K_d$ of an interaction between the first and second biomolecules is determined by determining the proportion of the first and second biomolecules bound to each other for a range of concentrations of the first and second biomolecules and determining the concentration of the first or second biomolecule required for half maximal binding of the first and second biomolecules.

13. The method according to claim 1, wherein the $K_{off}$ value for an interaction between the first and second biomolecules is determined by providing initial saturating concentrations of the first and second biomolecules, cleaving the second tether portion and monitoring any change in levels of bound first and second biomolecules.

14. The method according to claim 1, wherein said method further comprises providing a concentration of the first and second biomolecules around the $K_d$ of an interaction between the first and second biomolecules and determining the effect of a modulator on the portion of the first and the second biomolecules bound to each other.

15. The method according to claim 1, wherein the first and second tether portion are linked together to form a Y-shaped tether.

16. The method according to claim 1, wherein the first and second biomolecules are tethered to the surface at an inter-anchor distance so that the first and second biomolecules are closely adjacent to each other.

17. The method according to claim 16, wherein a range of inter-anchor distances produce a range of effective concentrations for the first and/or second biomolecules.

18. The method according to claim 1, wherein the second biomolecule is selected from a library.

19. The method according to claim 1, wherein the method further comprises changing said first and/or second persistence length of said first and/or second tethers of the first and/or second tether portion by chemical modification or physical association of the first and/or second tether portion to produce a range of effective concentrations for the first and/or second biomolecules.

20. The method according to claim 1, wherein the surface is provided by a solid support.

21. The method according to claim 20, wherein the at least one tether portion is tethered to the solid support by an oligonucleotide anchor.

22. The method according to claim 21, wherein the oligonucleotide anchor is set up as an array on the solid support.

23. The method according to claim 20, wherein the solid support is a glass slide.

24. The method according to claim 23, wherein the tether is set up as an array on the solid support.

25. The method according to claim 1, wherein the surface is provided by a microbead.

* * * * *

SEQUENCE LISTING

```
<160> NUMBER OF SEQ ID NOS: 21

<210> SEQ ID NO 1
<211> LENGTH: 40
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (30)..(40)
<223> OTHER INFORMATION: Region of single stranded DNA. No complementary
      strand present.

<400> SEQUENCE: 1
ctgcagaacc aggtgactgg tgaagcgagt gctgaagagc                              40

<210> SEQ ID NO 2
<211> LENGTH: 40
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(11)
<223> OTHER INFORMATION: Region of single stranded DNA. Residues from 5'
      to 3' strand missing. Only complementary strand present.

<400> SEQUENCE: 2
tgctgaagag ctgaagtcac ccagtcacct ggtgctgagc                              40

<210> SEQ ID NO 3
<211> LENGTH: 12
<212> TYPE: DNA
<213> ORGANISM: Artificial Sequence
<220> FEATURE:
<223> OTHER INFORMATION: Synthetic Construct

<400> SEQUENCE: 3
ccagtcacct gg                                                           12

<210> SEQ ID NO 4
<211> LENGTH: 48
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: Region of single stranded DNA which forms BstX1
      half site to allow ligation. Residues from 5' to 3' strand
      missing. Only complementary strand present.
<220> FEATURE:
<221> NAME/KEY: misc_feature
<222> LOCATION: (38)..(48)
<223> OTHER INFORMATION: Region of single stranded DNA. Residues from 5'
      to 3' strand missing. Only complementary strand present.

<400> SEQUENCE: 4
gtgactggtg aatgactacg agctagctta gagcgagtgc tgaagagc                    48

<210> SEQ ID NO 5
<211> LENGTH: 48
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (1)..(11)
<223> OTHER INFORMATION: Region of single stranded DNA. No complementary
      strand present.
<220> FEATURE:
<221> NAME/KEY: misc_feature
<222> LOCATION: (45)..(48)
<223> OTHER INFORMATION: Region of single stranded DNA which forms BstX1
      half site to allow ligation. No complementary strand present.

<400> SEQUENCE: 5
tgctgaagag ctgaagttag cgatcttaga tcagctacac ccagcaca                  48

<210> SEQ ID NO 6
<211> LENGTH: 48
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: Region of single stranded DNA which forms BstX1
      half site to allow ligation. Residues from 5' to 3' strand
      missing. Only complementary strand present.

<400> SEQUENCE: 6
gtgactggtg aatgactacg agctagctta gagcgagtgc tgaagagc                  48

<210> SEQ ID NO 7
<211> LENGTH: 37
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (34)..(37)
<223> OTHER INFORMATION: Region of single stranded DNA which forms a
      BstX1 half site to allow ligation. No complementary strand
      present.

<400> SEQUENCE: 7
tgaagttagc gatcttagat cagctacacc cagcaca                              37

<210> SEQ ID NO 8
<211> LENGTH: 48
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (38)..(48)
<223> OTHER INFORMATION: Region of single stranded DNA. Residues from 5'
      to 3' strand missing. Only complementary strand present.

<400> SEQUENCE: 8
gtgactggtg aatgactacg agctagctta gagcgagtgc tgaagagc                  48

<210> SEQ ID NO 9
<211> LENGTH: 48
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(11)
<223> OTHER INFORMATION: Region of single stranded DNA. No complementary
      strand present.
```

-continued

<400> SEQUENCE: 9
tgctgaagag ctgaagttag cgatcttaga tcagctacac ccagcaca                48

<210> SEQ ID NO 10
<211> LENGTH: 48
<212> TYPE: DNA
<213> ORGANISM: Artificial Sequence
<220> FEATURE:
<223> OTHER INFORMATION: Synthetic Construct

<400> SEQUENCE: 10
gtgactggtg aatgactacg agctagctta gagcgagtgc tgaagagc                48

<210> SEQ ID NO 11
<211> LENGTH: 37
<212> TYPE: DNA
<213> ORGANISM: Artificial Sequence
<220> FEATURE:
<223> OTHER INFORMATION: Synthetic Construct

<400> SEQUENCE: 11
tgaagttagc gatcttagat cagctacacc cagcaca                            37

<210> SEQ ID NO 12
<211> LENGTH: 29
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(29)
<223> OTHER INFORMATION: Complementary to SEQ ID NO 1. Shown 3' to 5' in
      Figure 13.

<400> SEQUENCE: 12
ctcgcttcac cagtcacctg gttctgcag                                     29

<210> SEQ ID NO 13
<211> LENGTH: 29
<212> TYPE: DNA
<213> ORGANISM: Artificial Sequence
<220> FEATURE:
<223> OTHER INFORMATION: Synthetic Construct

<400> SEQUENCE: 13
tgaagtcacc cagtcacctg gtgctgagc                                     29

<210> SEQ ID NO 14
<211> LENGTH: 40
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(40)
<223> OTHER INFORMATION: Complementary to SEQ ID NO 13. Shown 3' to 5'
      in Figure 13.

<400> SEQUENCE: 14
gctcagcacc aggtgactgg gtgacttcag ctcttcagca                         40

<210> SEQ ID NO 15
<211> LENGTH: 12
<212> TYPE: DNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(12)
<223> OTHER INFORMATION: Palindrome. Figure 17

<400> SEQUENCE: 15
ccaggtgact gg                                                          12

<210> SEQ ID NO 16
<211> LENGTH: 33
<212> TYPE: DNA
<213> ORGANISM: Artificial Sequence
<220> FEATURE:
<223> OTHER INFORMATION: Synthetic Construct

<400> SEQUENCE: 16
ctggtgaatg actacgagct agcttagagc gag                                   33

<210> SEQ ID NO 17
<211> LENGTH: 48
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(48)
<223> OTHER INFORMATION: Complementary to SEQ ID NOs 4, 17, and 20.
      Shown 3' to 5' in Figure 19A-D.

<400> SEQUENCE: 17
gctcttcagc actcgctcta agctagctcg tagtcattca ccagtcac                   48

<210> SEQ ID NO 18
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(33)
<223> OTHER INFORMATION: Complementary to SEQ ID NO 7. Shown 3' to 5' in
      Figures 19A and 19B.

<400> SEQUENCE: 18
ctgggtgtag ctgatctaag atcgctaact tca                                   33

<210> SEQ ID NO 19
<211> LENGTH: 37
<212> TYPE: DNA
<213> ORGANISM: Artificial Sequence
<220> FEATURE:
<223> OTHER INFORMATION: Synthetic Construct

<400> SEQUENCE: 19
gtgactggtg aatgactacg agctagctta gagcgag                               37

<210> SEQ ID NO 20
<211> LENGTH: 37
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

-continued

```
<222> LOCATION: (1)..(37)
<223> OTHER INFORMATION: Complementary to SEQ ID NO 5 and 7. Shown 3' to
      5' in Figures 19C and 19D.

<400> SEQUENCE: 20
tgtgctgggt gtagctgatc taagatcgct aacttca                                    37

<210> SEQ ID NO 21
<211> LENGTH: 44
<212> TYPE: DNA
<213> ORGANISM: Artificial Sequence
<220> FEATURE:
<223> OTHER INFORMATION: Synthetic Construct

<400> SEQUENCE: 21
ctggtgaatg actacgagct agcttagagc gagtgctgaa gagc                            44
```